United States Patent
Sato et al.

(10) Patent No.: US 9,902,979 B2
(45) Date of Patent: Feb. 27, 2018

(54) METHOD FOR PRODUCING AMBREIN

(71) Applicant: Niigata University, Niigata (JP)

(72) Inventors: Tsutomu Sato, Niigata (JP); Daijiro Ueda, Niigata (JP); Tsutomu Hoshino, Niigata (JP)

(73) Assignee: Niigata University (JP)

( * ) Notice: Subject to any disclaimer, the term of this patent is extended or adjusted under 35 U.S.C. 154(b) by 0 days.

(21) Appl. No.: 14/916,216

(22) PCT Filed: Aug. 12, 2014

(86) PCT No.: PCT/JP2014/071333
§ 371 (c)(1),
(2) Date: Mar. 3, 2016

(87) PCT Pub. No.: WO2015/033746
PCT Pub. Date: Mar. 12, 2015

(65) Prior Publication Data
US 2016/0304911 A1    Oct. 20, 2016

(30) Foreign Application Priority Data

Sep. 5, 2013   (JP) .................................. 2013-184143

(51) Int. Cl.
*C12P 7/22* (2006.01)
*C12N 9/90* (2006.01)
*C12N 9/88* (2006.01)
*C12P 7/02* (2006.01)

(52) U.S. Cl.
CPC .................. *C12P 7/22* (2013.01); *C12N 9/88* (2013.01); *C12N 9/90* (2013.01); *C12P 7/02* (2013.01); *C12Y 402/0313* (2015.07); *C12Y 504/99017* (2013.01)

(58) Field of Classification Search
None
See application file for complete search history.

(56) References Cited

U.S. PATENT DOCUMENTS

2009/0205060 A1* 8/2009 Schalk .................... C12N 9/88
                                                         800/13
2016/0168595 A1* 6/2016 Janssen ................... C12P 5/007
                                                         435/166

FOREIGN PATENT DOCUMENTS

JP      H10-236996 A      9/1998

OTHER PUBLICATIONS

Siedenburg et al., Squalene-hopene cyclases, App. Environ. Microbiol., 2011, 77, 3905-15.*
Hoshino et al., Squalene-hopene cyclase: catalytic mechanism and substrate recognition, Chem. Commun., 2002, 4, 291-301.*
Tetrahedron Asymmetry, (2006) vol. 17, pp. 3037-3045.
Biosci. Biotechnol. Biochem., (1999) vol. 63, pp. 2189-2198.
Biosci. Biotechnol. Biochem., (2001) vol. 65, pp. 2233-2242.
Biosci. Biotechnol. Biochem., (2002) vol. 66, pp. 1660-1670.
J. Am. Chem. Soc., (2011) vol. 133, pp. 17540-17543.

* cited by examiner

*Primary Examiner* — Robert B Mondesi
*Assistant Examiner* — Todd M Epstein
(74) *Attorney, Agent, or Firm* — Banner & Witcoff, Ltd.

(57) ABSTRACT

Provided is a method for producing ambrein, comprising reacting tetraprenyl-β-curcumene cyclase with 3-deoxyachilleol A to obtain ambrein.

10 Claims, No Drawings

METHOD FOR PRODUCING AMBREIN

RELATED APPLICATION DATA

This application is a National Stage Application under 35 U.S.C. 371 of co-pending PCT application number PCT/JP2014/071333 designating the United States and filed Aug. 12, 2014; which claims the benefit of JP application number 2013-184143 and filed Sep. 5, 2013 each of which are hereby incorporated by reference in their entireties.

TECHNICAL FIELD

The present invention relates to a method for producing ambrein.

BACKGROUND ART

Ambergris is a high grade perfume which has been used from around the seventh century, and has been also used as a Chinese medicinal drug. Ambergris is considered to be formed by sperm whales due to lithification of indigestibles of foods (octopuses, squids, or the like) by gastrointestinal secretions and excreted therefrom. The detailed production mechanism thereof, however, is unknown. The principal component of ambergris is ambrein, and it is considered that ambrein is subjected to oxidative decomposition by sunlight and oxygen while the ambergris is floating on the ocean's surface, thereby producing compounds having a variety of fragrances.

Although ambrein, the principal component of ambergris, is used as perfumes or pharmaceuticals, it is impossible to obtain a large amount of ambrein as a natural product. A variety of organic synthesis methods have thus been proposed.

For example, as a method of producing (+)-ambrein easily, efficiently, and inexpensively, Japanese Patent Application Laid-Open (JP-A) No. H10-236996 discloses a method comprising a step of producing a new sulfonic acid derivative from ambrenolide and coupling therewith an optically active γ-cyclogeranyl halide.

*Tetrahedron Asymmetry*, (2006) Vol. 17, pp. 3037-3045 discloses a method of obtaining ambrein by a convergent synthesis using a Julia coupling reaction between 2-((1R,2R,4αS,8αS)-2-(methoxymethoxy)-2,5,5,8α-tetramethyl decahydronaphthalene-1-yl)acetaldehyde synthesized from (±)(5,5,8α-trimethyloctahydro-1H-spiro[naphthalene-2,2'-oxirane]-1-yl)methanol and 5-((4-((S)-2,2-dimethyl-6-methylenecyclohexyl)butane-2-yl)sulfonyl)-1-phenyl-1H-tetrazole synthesized from (±)methyl 6-hydroxy-2,2-dimethyl cyclohexanecarboxylate.

A method in which 3-deoxyachilleol A which is a monocyclic triterpene is obtained from squalene by using a mutant enzyme (D377C, D377N, Y420H, Y420W, or the like) of a squalene-hopene cyclase is also known (*Biosci. Biotechnol. Biochem.*, (1999) Vol. 63, pp. 2189-2198, *Biosci. Biotechnol. Biochem.*, (2001) Vol. 65, pp. 2233-2242, and *Biosci. Biotechnol. Biochem.*, (2002) Vol. 66, pp. 1660-1670).

It is also reported that tetraprenyl-β-curcumene cyclase is a bifunctional enzyme which is involved in two reactions: a reaction in which a tetracyclic $C_{35}$ terpenol is produced from tetraprenyl-β-curcumene; and a reaction in which a bicyclic triterpene is produced from squalene (*J. Am. Chem. Soc.*, (2011) Vol. 133, pp. 17540-17543).

SUMMARY OF INVENTION

Technical Problem

Since conventional organic synthesis methods of ambrein involve many synthesis stages, the reaction systems are complex, and therefore commercialization thereof has not been accomplished. In addition, no specific enzyme that is involved in production of ambrein is known.

Accordingly, an object in the invention is to provide a method for producing ambrein in which ambrein can be produced more easily than conventionally known organic synthesis methods.

Solution to Problem

The invention is as follows:

[1] A method for producing ambrein, comprising reacting a tetraprenyl-β-curcumene cyclase with 3-deoxyachilleol A to obtain ambrein.

[2] The method for producing ambrein according to [1], wherein the tetraprenyl-β-curcumene cyclase is derived from a bacterium of the genus *Bacillus*.

[3] The method for producing ambrein according to [1] or [2], wherein the tetraprenyl-β-curcumene cyclase is derived from any one of *Bacillus megaterium*, *Bacillus subtilis* or *Bacillus licheniformis*.

[4] The method for producing ambrein according to any one of [1] to [3], further comprising reacting a mutant squalene-hopene cyclase, which can produce 3-deoxyachilleol A from squalene, with squalene to obtain 3-deoxyachilleol A.

[5] The method for producing ambrein according to [4], wherein the mutant squalene-hopene cyclase has an amino acid substitution at at least one position selected from the group consisting of position 377, position 420, position 607, and position 612 in the amino acid sequence represented by SEQ ID NO:1.

[6] The method for producing ambrein according to [4] or [5], wherein the mutant squalene-hopene cyclase has the amino acid sequence represented by any one of SEQ ID NO:2, SEQ ID NO:3, SEQ ID NO:4, SEQ ID NO:5, SEQ ID NO:6, SEQ ID NO:7, and SEQ ID NO:8.

[7] The method for producing ambrein according to any one of [1] to [6], wherein the tetraprenyl-β-curcumene cyclase has the amino acid sequence represented by any one of SEQ ID NO:16, SEQ ID NO:17, and SEQ ID NO:18.

Effects of Invention

According to the invention, there is provided a method for producing ambrein in which ambrein can be produced more easily than conventionally known organic synthesis methods.

DESCRIPTION OF EMBODIMENTS

The term "step" herein includes not only independent steps. Even when a step cannot be clearly distinguished from other steps, the step is included in this term as long as the expected purpose of the step can be achieved.

Further, each numerical range represented using "to" herein means the range having the numerical values described before and after the "to" as the minimum value and the maximum value, respectively.

When the composition contains a plurality of substances corresponding to the each component, the amount of the each component in the composition herein means the total amount of the plurality of substances contained in the composition unless otherwise specified.

In the invention, each amino acid residue in an amino acid sequence may be represented by the single-letter code (for example, "G" represents a glycine residue) or three-letter code (for example, "Gly" represents a glycine residue), which are well known in the art.

In the invention, "%" as used in relation to the amino acid sequence of a protein or a polypeptide is based on the number of amino acid residues, unless otherwise specified.

In the following, embodiments in the invention will now be described. These descriptions and Examples are for illustration of the invention and should not limit the scope of the present invention.

The method of producing ambrein of the present invention is a method comprising: reacting a tetraprenyl-β-curcumene cyclase with 3-deoxyachilleol A to obtain ambrein.

In the invention, ambrein can be easily produced since tetraprenyl-β-curcumene cyclase is reacted with 3-deoxyachilleol A to obtain ambrein.

Although tetraprenyl-β-curcumene cyclase has been known to be an enzyme which produces a bicyclic terpenol from squalene which is a $C_{30}$ linear unsaturated hydrocarbon, it has been found that 3-deoxyachilleol A which comprises a monocycle at one end can be employed as a substrate. It has been also found that, when 3-deoxyachilleol A is utilized as a substrate, a tetraprenyl-β-curcumene cyclase selectively forms a ring on the end of the 3-deoxyachilleol A on which a ring has not been formed to produce a compound which is cyclized at both ends. The invention has been made based on these findings. Due to the above-described activity of tetraprenyl-β-curcumene cyclase, ambrein can be produced easily using 3-deoxyachilleol A comprising a monocycle on one end as a material by using one enzyme.

The method for producing ambrein in the invention comprises: reacting tetraprenyl-β-curcumene cyclase with 3-deoxyachilleol A to obtain ambrein (hereinafter referred to as an "ambrein production step"). The method comprises other steps as needed.

Ambrein is (1R,4aα)-1-[(E)-6-[(S)-2,2-dimethyl-6-methylenecyclohexyl]-4-methyl-3-hexenyl]decahydro-2,5,5,8aβ-tetramethylnaphthalene-2α-al, and a compound which is cyclized at both ends. Ambrein has a composition formula of $C_{30}H_{52}O$ and a molecular weight of 428.745, which is a triterpene alcohol having the following structure (CAS registration number:473-03-0):

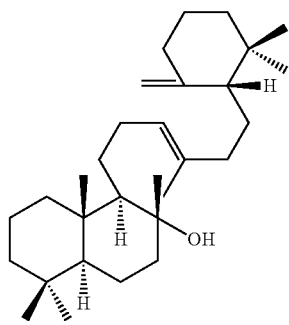

In the method for producing ambrein in the invention, 3-deoxyachilleol A is utilized as a substrate of tetraprenyl-β-curcumene cyclase.

3-deoxyachilleol A is (S)-1,1-dimethyl-3-methylene-2-((3E,7E,11E)-3,8,12,16-tetramethyl heptadeca-3,7,11,15-tetraen-1-yl)cyclohexane, and a compound which is cyclized at one end. 3-deoxyachilleol A has a composition formula of $C_{30}H_{50}$, and the following structure. This compound is used in the invention as a material for producing ambrein. A method of obtaining 3-deoxyachilleol A is not particularly restricted. 3-deoxyachilleol A may be obtained by chemical synthesis, or may be obtained from a known compound by using enzyme reaction.

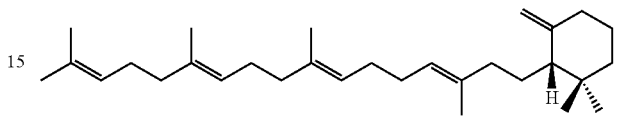

The production method in the invention preferably further comprises: reacting a mutant squalene-hopene cyclase with squalene to obtain 3-deoxyachilleol A (hereinafter, referred to as a "3-deoxyachilleol A production step"). This makes it possible to efficiently and easily produce ambrein through two enzyme reactions using a mutant squalene-hopene cyclase and a tetraprenyl-β-curcumene cyclase by using inexpensive squalene as a material.

[3-Deoxyachilleol A Production Step]

In a 3-deoxyachilleol A production step, a mutant squalene-hopene cyclase, which can produce 3-deoxyachilleol A from squalene, is reacted with squalene to obtain 3-deoxyachilleol A. The term "mutant squalene-hopene cyclase" herein refers to a mutant squalene-hopene cyclase, which can produce 3-deoxyachilleol A from squalene, unless otherwise specified.

In the invention, a mutant squalene-hopene cyclase is an enzyme that is obtained by modifying wild-type squalene-hopene cyclase and that can produce 3-deoxyachilleol A from squalene. A wild-type squalene-hopene cyclase is known to be an enzyme (ECS. 4. 99. -) which cyclizes squalene to produce a pentacyclic hopene or hopanol, which is widely found in a prokaryote such as the genus *Alicyclobacillus*, the genus *Zymomonas*, or the genus *Bradyrhizobium*. The amino acid sequence of a wild-type squalene-hopene cyclase is known. For example, the amino acid sequence (SEQ ID NO:1) (Table 1) of wild-type squalene-hopene cyclase of *Alicyclobacillus acidocaldarius* is shown in GenBank Accession No.: AB007002.

TABLE 1

| Wild-type squalene-hopene cyclase derived from *Alicyclobacillus acidocaldarius* |
|---|
| MAEQLVEAPA YARTLDRAVE YLLSCQKDEG YWWGPLLSNV |
| TMEAEYVLLC HILDRVDRDR MEKIRRYLLH EQREDGTWAL |
| YPGGPPDLDT TIEAYVALKY IGMSRDEEPM QKALRFIQSQ |
| GGIESSRVFT RMWLALVGEY PWEKVPMVPP EIMFLGKRMP |
| LNIYEFGSWA RATVVALSIV MSRQPVFPLP ERARVPELYE |
| TDVPPRRRGA KGGGGWIFDA LDRALHGYQK LSVHPFRRAA |
| EIRALDWLLE RQAGDGSWGG IQPPWFYALI ALKILDMTQH |
| PAFIKGWEGL ELYGVELDYG GWMFQASISP VWDTGLAVLA |
| LRAAGLPADH DRLVKAGEWL LDRQITVPGD WAVKRPNLKP |

TABLE 1-continued

Wild-type squalene-hopene cyclase derived from
Alicyclobacillus acidocaldarius

```
GGFAFQFDNV YYPDVDDTAV VVWALNTLRL PDERRRRDAM

TKGFRWIVGM QSSNGGWGAY DVDNTSDLPN HIPFCDFGEV

TDPPSEDVTA HVLECFGSFG YDDAWKVIRR AVEYLKREQK

PDGSWFGRWG VNYLYGTGAV VSALKAVGID TREPYIQKAL

DWVEQHQNPD GGWGEDCRSY EDPAYAGKGA STPSQTAWAL

MALIAGGRAE SEAARRGVQY LVETQRPDGG WDEPYYTGTG

FPGDFYLGYT MYRHVFPTLA LGRYKQAIER R
```

The mutant squalene-hopene cyclase is an enzyme which contains a mutation in the amino acid sequence of a wild-type squalene-hopene cyclase and which has an activity by which 3-deoxyachilleol A having a monocycle can be produced from squalene. It is known that, in a case that a mutation is contained in the amino acid sequence of a wild-type squalene-hopene cyclase, an incomplete cyclization reaction occurs, and that a monocycle compound can be produced when squalene is reacted therewith while a wild-type squalene-hopene cyclase without a mutation produces a pentacyclic compound.

From the viewpoint of production efficiency of 3-deoxyachilleol A, the mutant squalene-hopene cyclase is preferably a mutant squalene-hopene cyclase having an amino acid substitution(s) at least one site selected from the group consisting of position 377, position 420, position 607, and position 612 in the amino acid sequence represented by SEQ ID NO:1, more preferably a mutant squalene-hopene cyclase having a mutation(s) at one or two sites selected from the group consisting of position 377, position 420, position 607, and position 612 in the amino acid sequence represented by SEQ ID NO:1, and still more preferably a mutant squalene-hopene cyclase having a mutation at any one of sites selected from the group consisting of position 377, position 420, position 607, and position 612 in the amino acid sequence represented by SEQ ID NO:1.

The above-described mutation sites in the mutant squalene-hopene cyclase are relative ones. For example, "position 377" is actually position 376 when one amino acid residue on the N terminal side of the position 377 is deleted. When the amino acid sequence of a wild-type squalene-hopene cyclase includes a species-specific variation irrespective of the function of squalene-hopene cyclase itself depending on the species, the above-described mutation sites should be read as sites on which an alignment has been performed in a known method in the art.

Amino acid substitution in a mutant squalene-hopene cyclase is that an amino acid residue of a wild-type squalene-hopene cyclase is substituted with another amino acid residue. The other amino acid residue with which the amino acid residue of the wild-type squalene-hopene cyclase is to be substituted may be any amino acid residue as long as it is an amino acid residue by which a mutant squalene-hopene cyclase after the substitution can produce 3-deoxyachilleol A from squalene.

The mutation site and the substituted amino acid of a mutant squalene-hopene cyclase are preferably the following mutation site in the amino acid sequence represented by SEQ ID NO:1 and substituted amino acid.

(i) The aspartic acid residue (D) at position 377 is substituted with a cysteine residue (C) or an asparagine residue (N).

(ii) The tyrosine residue (Y) at position 420 is substituted with a histidine residue (H) or a tryptophan residue (W).

(iii) The leucine residue (L) at position 607 is substituted with a phenylalanine residue (F) or a tryptophan residue (W).

(iv) The tyrosine residue (Y) at position 612 is substituted with an alanine residue (A).

The mutant squalene-hopene cyclase is preferably an enzyme having at least one substitution selected from the group consisting of the above-described (i) to (iv) in the amino acid sequence represented by SEQ ID NO:1, more preferably an enzyme having one or two substitutions selected from the group consisting of the above-described (i) to (iv) in the amino acid sequence represented by SEQ ID NO:1, and further preferably an enzyme having one substitution selected from the group consisting of the above-described (i) to (iv) in the amino acid sequence represented by SEQ ID NO:1.

The mutant squalene-hopene cyclase may have an amino acid sequence wherein one or more amino acid residues are substituted, deleted, inserted, or added at a site(s) in the amino acid sequence of the wild-type squalene-hopene cyclase other than the above-described mutation sites as long as a function of producing 3-deoxyachilleol A from squalene is maintained. In this case, the number of the one or several amino acid residues which is/are substituted, deleted, inserted, or added varies depending on the positions of the amino acid residue(s) in the spatial structure of the protein and the types of the amino acid residue(s) or the like. Specifically, the number thereof is preferably 1 to 20, more preferably 1 to 10, and further preferably 1 to 5.

The origin of the mutant squalene-hopene cyclase is not particularly limited, and the mutant squalene-hopene cyclase is preferably derived from, for example, a bacterium of the genus *Alicyclobacillus*, a bacterium of the genus *Zymomonas*, or a bacterium of the genus *Bradyrhizobium*. From the viewpoint of enzyme activity, the mutant squalene-hopene cyclase is more preferably a mutant squalene-hopene cyclase derived from a bacterium of the genus *Alicyclobacillus*, and particularly preferably a mutant squalene-hopene cyclase derived from *Alicyclobacillus acidocaldarius* among others.

From the viewpoint of enzyme activity, the mutant squalene-hopene cyclase is preferably polypeptides A to G (SEQ ID NOs:2 to 8) listed below. In Table 2, the amino acid residues of the polypeptides are the same as the amino acid residue in the amino acid sequence represented by SEQ ID NO:1 except for the mutations represented by "mutation".

TABLE 2

| Polypeptide Name | Origin | Mutation | SEQ ID No. |
| --- | --- | --- | --- |
| A | *Alicyclobacillus acidocaldarius* | D377C | 2 |
| B | *Alicyclobacillus acidocaldarius* | D377N | 3 |
| C | *Alicyclobacillus acidocaldarius* | Y420H | 4 |
| D | *Alicyclobacillus acidocaldarius* | Y420W | 5 |
| E | *Alicyclobacillus acidocaldarius* | L607F | 6 |
| F | *Alicyclobacillus acidocaldarius* | L607W | 7 |
| G | *Alicyclobacillus acidocaldarius* | Y612A | 8 |

The polypeptides A to G which are mutant squalene-hopene cyclases respectively encompass polypeptides which have the amino acid sequences represented by SEQ ID NOs:2 to 8 wherein one or several amino acid residues are substituted, deleted, inserted, or added, and in which a function of producing 3-deoxyachilleol A from squalene is maintained. The number of amino acid residues which are substituted, deleted, inserted, or added in each of the amino acid sequences represented by SEQ ID NOs:2 to 8 is, specifically, preferably 1 to 20, more preferably 1 to 10, and further preferably 1 to 5.

The polypeptides A to G which are mutant squalene-hopene cyclases respectively encompass polypeptides which have sequence identity of, for example, 80% or higher, preferably 90% or higher, more preferably 95% or higher, more preferably 97% or higher, more preferably 98% or higher, and particular preferably 99% or higher, to the whole amino acid sequences each represented by SEQ ID NOs:2 to 8, and in which a function of producing 3-deoxyachilleol A from squalene is maintained.

A polynucleotide which can express a mutant squalene-hopene cyclase can be obtained on the basis of information on the sequence of the wild-type mutant squalene-hopene cyclase. Examples of the polynucleotide which can express a mutant squalene-hopene cyclase include polynucleotides A to G having the base sequences represented by SEQ ID NOs:9 to 15 (Table 3). In Table 3, the base sequences are the same as the base sequence (GenBank Accession No.: AB007002) of the wild-type squalene-hopene cyclase gene of *Alicyclobacillus acidocaldarius* except for the sites listed in "mutation site".

TABLE 3

| Polynucleotide Name | Mutation | Mutation Site | Base | SEQ ID No. |
|---|---|---|---|---|
| A | D377C | 1129-1131 | gac→tgc | 9 |
| B | D377N | 1129-1131 | gac→aac | 10 |
| C | Y420H | 1258-1260 | tac→cac | 11 |
| D | Y420W | 1258-1260 | tac→tgg | 12 |
| E | L607F | 1819-1821 | ctc→ttc | 13 |
| F | L607W | 1819-1821 | ctc→tgg | 14 |
| G | Y612A | 1834-1836 | tac→gcc | 15 |

The polynucleotides A to G encompass respectively polynucleotides which have the base sequences represented by SEQ ID NOs:9 to 15 wherein one or several bases are substituted, deleted, inserted, or added, and which encode a polypeptide in which a function of producing 3-deoxychilleol A from squalene is maintained. The number of bases which are substituted, deleted, inserted, or added in each of the base sequences represented by SEQ ID NOs:9 to 15 is, specifically, preferably 1 to 20, more preferably 1 to 10, and further preferably 1 to 5.

The polynucleotides A to G respectively encompass polynucleotides which have sequence identity of, for example, 80% or higher, preferably 90% or higher, more preferably 95% or higher, more preferably 97% or higher, more preferably 98% or higher, and particular preferably 99% or higher, to the whole base sequences each represented by SEQ ID NOs:9 to 15, and which encode polypeptides in which a function of producing 3-deoxyachilleol A from squalene is maintained.

The polynucleotides A to G respectively encompass polynucleotides which hybridize with complementary strands of the base sequences represented by SEQ ID NOs:9 to 15 under stringent conditions, and which encode a polypeptide in which a function of producing 3-deoxyachilleol A from squalene.

Hybridization can be performed according to a known method or a method according to a known method, such as a method described in *Molecular Cloning* 3rd (J. Sambrook et al., Cold Spring Harbor Lab. Press, 2001). The stringent conditions mean conditions under which a specific hybrid is formed while nonspecific hybrids are not formed. Typical examples of the stringent conditions include conditions under which hybridization is performed with a potassium concentration of about 25 mM to about 50 mM and a magnesium concentration of about 1.0 mM to about 5.0 mM. In the invention, examples of the conditions include conditions under which hybridization is performed in Tris-HCl buffer (pH 8.6), 25 mM KCl and 1.5 mM $MgCl_2$, but the conditions are not limited thereto. Other examples of the stringent conditions include those described in *Molecular Cloning* 3rd (J. Sambrook et al., Cold Spring Harbor Lab. Press, 2001). Those skilled in the art can easily select stringent conditions by changing the conditions of the hybridization reaction such as the concentrations of salts condition of the hybridization reaction liquid.

A recombinant vector which is used for expressing a polynucleotide which encodes a mutant squalene-hopene cyclase is not particularly restricted, and examples thereof include a vector which can be expressed by *Escherichia coli* such as pET-3a, a vector which can be expressed by *Bacillus subtilis* such as pHT01, and a vector which can be expressed by yeast such as pYES2. By introducing a polynucleotide encoding a mutant squalene-hopene cyclase into such a vector, an enzyme expression vector can be obtained. A host bacterium which is a target for introducing an enzyme expression vector can be appropriately selected according to the type of a recombinant vector to be used, and examples thereof include *Escherichia coli* such as BL21 (DE3), *Bacillus subtilis* such as strain 168, and yeast such as *Saccharomyces cerevisiae*.

The recombinant vector may contain, as needed, a promoter, a splicing signal, a poly(A) addition signal, a selection marker, a ribosome binding sequence (SD sequence), a terminator such as NOS, and/or the like. As the selection marker, a known one such as an antibiotic resistance gene such as a kanamycin resistance gene, an ampicillin resistance gene or a tetracycline resistance gene is used without particular restriction.

The recombinant vector may contain a reporter gene for confirming that an objective gene is introduced. Examples of such a reporter gene include a GUS (β-glucuronidase) gene, a luciferase gene, and a GFP (green fluorescent protein) gene.

The mutant squalene-hopene cyclase is produced by culturing a transformant that is obtained by introducing an enzyme expression vector into a bacterium. A culture medium used for culturing a transformant may be a culture medium which is usually used, and is appropriately selected according to the type of a host. For example, when *Escherichia coli* are cultured, an LB medium or the like is used. An antibiotic may be added to a culture medium according to the type of a selection marker.

The mutant squalene-hopene cyclase may be obtained by extraction followed by purification from a culture medium which has been obtained by culturing a transformant capable of expressing the enzyme. An extraction liquid containing the enzyme, which has been extracted from a transformant in a culture medium, may be used as it is. As a method of extracting an enzyme from a transformant, a known method may be applied. A step of extracting an enzyme may comprise, for example, crushing a transformant in an extraction solvent and separating cell contents from crushed pieces of the transformant. The obtained cell contents contain a target mutant squalene-hopene cyclase. Cell contents obtained by extracting from a cell and separating from crushed pieces of the cell are herein referred to as a "cell-free extract".

Regarding a method of crushing a transformant, a method of separating cell contents from crushed pieces of a microorganism, the composition of an extraction solvent, and pH conditions, those identical to the description of the ambrein production step described below are applied as they are.

Mutant squalene-hopene cyclases may be used singly, or in combination of two or more kinds thereof.

The conditions of a reaction between a mutant squalene-hopene cyclase and squalene are not particularly restricted as long as the conditions are such that an enzyme reaction can be proceeded. For example, the reaction temperature and the reaction time may be appropriately selected based on the activity of a mutant squalene-hopene cyclase or the like. From the viewpoint of reaction efficiency, the reaction temperature and the reaction time may be, for example, from 4° C. to 100° C. and from 0.1 hour to 48 hours, and preferably 30° C. to 60° C. and 16 hours to 24 hours. From the viewpoint of reaction efficiency, the pH is, for example, from 3 to 10, and preferably from 6 to 8.

A reaction solvent is not particularly restricted as long as the reaction solvent does not inhibit the enzyme reaction, and a buffer or the like which is usually used can be used. For example, the same solvent as an extraction solvent which is used in a step of extracting the enzyme can be used. An extraction liquid (for example, cell-free extract) containing a mutant squalene-hopene cyclase may be used as it is as an enzyme liquid in the reaction.

From the viewpoint of reaction efficiency, in a production reaction of 3-deoxyachilleol A, the concentration ratio between a mutant squalene-hopene cyclase and squalene which is the substrate thereof in a production reaction of 3-deoxyachilleol A is preferably from 10 to 10000, more preferably from 100 to 5000, still more preferably from 1000 to 3000, and still further preferably from 1000 to 2000 in terms of the molar concentration ratio (substrate/enzyme) of the substrate to the enzyme.

From the viewpoint of reaction efficiency, the concentration of squalene to be used for an enzyme reaction is preferably from 0.000001% by mass to 0.002% by mass, and more preferably from 0.00001% by mass to 0.0002% by mass based on the total mass of the reaction solvent.

3-deoxyachilleol A obtained by a reaction using a mutant squalene-hopene cyclase can be purified by a known method, and can then be subjected to a reaction with a tetraprenyl-β-curcumene cyclase.

The purification method of 3-deoxyachilleol A is not particularly restricted as long as 3-deoxyachilleol A in a reaction liquid can be taken out, and a purification method which is usually used may be appropriately selected. Specific examples of the purification method include solvent extraction, recrystallization, distillation, column chromatography, and high performance liquid chromatography (HPLC).

A step of reaction between a mutant squalene-hopene cyclase and squalene may be repeated a plurality of times. This can increase the yield of 3-deoxyachilleol A. In a case that a plurality of reaction steps are repeated, the purification method may comprise: a step of recharging squalene to be the substrate; a step of recovering and purifying a reaction product in a reaction liquid after deactivating the enzyme by a known method; and the like. In a case that squalene is recharged, a charging point in time and the amount of charging of squalene can be appropriately set according to the concentration of the mutant squalene-hopene cyclase in the reaction liquid, the amount of the substrate remained in the reaction liquid, or the like.

[Ambrein Production Step]

In an ambrein production step, a tetraprenyl-β-curcumene cyclase is reacted with 3-deoxyachilleol A to obtain ambrein.

A tetraprenyl-β-curcumene cyclase, which is classified as belonging to EC 4.2.1.129, is an enzyme capable of catalyzing a reaction which produces baciterpenol A from water and tetraprenyl-β-curcumene or a reaction which produces 8α-hydroxypolypoda-13,17,21-triene from squalene.

A tetraprenyl-β-curcumene cyclase is known as an enzyme which a bacterium such as the genus *Bacillus* produces. From the viewpoint of reaction efficiency, a tetraprenyl-β-curcumene cyclase is preferably derived from a bacterium of the genus *Bacillus*.

The tetraprenyl-β-curcumene cyclase derived from a bacterium of the genus *Bacillus* is preferably an enzyme derived from *Bacillus megaterium*, *Bacillus subtilis*, *Bacillus licheniformis*, or the like, and from the viewpoint of reaction efficiency, it is more preferably an enzyme derived from *Bacillus megaterium* or *Bacillus subtilis*, and particularly preferably an enzyme derived from *Bacillus megaterium*.

The amino acid sequence of a tetraprenyl-β-curcumene cyclase of *Bacillus* bacteria is known.

The amino acid sequence of a tetraprenyl-β-curcumene cyclase derived from *Bacillus megaterium* is shown in GenBank Accession No.: ADF38987 (SEQ ID NO:16) (Table 4).

The amino acid sequence of a tetraprenyl-β-curcumene cyclase derived from *Bacillus subtilis* is shown in GenBank Accession No.: AB618206 (SEQ ID NO:17) (Table 5).

The amino acid sequence of a tetraprenyl-β-curcumene cyclase derived from *Bacillus licheniformis* is shown in GenBank Accession No.: AAU41134 (SEQ ID NO:18) (Table 6).

From the viewpoint of reaction efficiency, the tetraprenyl-β-curcumene cyclase is preferably a tetraprenyl-β-curcumene cyclase having the amino acid sequence represented by SEQ ID NO:16, SEQ ID NO:17, or SEQ ID NO:18, and more preferably a tetraprenyl-β-curcumene cyclase having the amino acid sequence represented by SEQ ID NO:16.

TABLE 4

Tetraprenyl-β-curcumene Cyclase Derived from
*Bacillus megaterium*

MIILLKEVQL EIQRRIAYLR PTQKNDGSFR YCFETGVMPD

AFLIMLLRTF DLDKEVLIKQ LTERIVSLQN EDGLWTLFDD

EEHNLSATIQ AYTALLYSGY YQKNDRILRK AERYIIDSGG

ISRAHFLTRW MLSVNGLYEW PKLFYLPLSL LLVPTYVPLN

FYELSTYARI HFVPMMVAGN KKFSLTSRHT PSLSHLDVRE

QKQESEETTQ ESRASIFLVD HLKQLASLPS YIHKLGYQAA

ERYMLERIEK DGTLYSYATS TFFMIYGLLA LGYKKDSFVI

QKAIDGICSL LSTCSGHVHV ENSTSTVWDT ALLSYALQEA

GVPQQDPMIK GTTRYLKKRQ HTKLGDWQFH NPNTAPGGWG

FSDINTNNPD LDDTSAAIRA LSRRAQTDTD YLESWQRGIN

WLLSMQNKDG GFAAFEKNTD SILFTYLPLE NAKDAATDPA

TABLE 4-continued

Tetraprenyl-β-curcumene Cyclase Derived from
Bacillus megaterium

TADLTGRVLE CLGNFAGMNK SHPSIKAAVK WLFDHQLDNG

SWYGRWGVCY IYGTWAAITG LRAVGVSASD PRIIKAINWL

KSIQQEDGGF GESCYSASLK KYVPLSFSTP SQTAWALDAL

MTICPLKDRS VEKGIKFLLN PNLTEQQTHY PTGIGLPGQF

YIQYHSYNDI FPLLALAHYA KKHSS

TABLE 5

Tetraprenyl-β-curcumene Cyclase Derived from
Bacillus subtilis

MGTLQEKVRR YQKKTIAELK NRQNADGSWT FCFEGPIMTN

SFFILLLTSL DEGENEKELI SALAAGIREK QQPDGTFINY

PDETSGNITA TVQGYVGMLA SGCFHRSDPH MRKAEQSIIS

HGGLRHVHFM TKWMLAVNGL YPWPVLYLPL SLMALPPTLP

VHFYQFSAYA RIHFAPMAVT LNQRFVLKNR NIPSLRHLDP

HMTKNPFTWL RSDAFEERDL TSIWSHWNRI FHAPFAFQQL

GLQTAKTYML DRIEKDGTLY SYASATIFMV YSLLSLGVSR

YSPVIKRAIN GIKSLMTKCN GIPYLENSTS TVWDTALISY

ALQKNGVTET DGSITKAAAY LLERQHTKRA DWSVKNPSAA

PGGWGFSNIN TNNPDCDDTA AVLKAIPHSY SPSAWERGVS

WLLSMQNNDG GFSAFEKNVN HPLIRLLPLE SAEDAAVDPS

TADLTGRVLH FLGEKAGFTE KHQHIQRAVN WLFEHQEQNG

SWYGRWGVCY IYGTWAALTG MHACEVDRKH PAIQKALRWL

KSIQHDDGSW GESCNSAEVK TYVPLHKGTI VQTAWALDAL

LTYESSEHPS VVKGMQYLTD SSYHGADSLA YPAGIGLPKQ

FYIRYHSYPY VFSLLAVGKY LNSIEKETAN ET

TABLE 6

Tetraprenyl-β-curcumene Cyclase Derived from
Bacillus licheniformis

MTDSFFILML TSLGDQDSSL IASLAERIRS RQSEDGAFRN

HPDERAGNLT ATVQGYTGML ASGLYDRKAP HMQKAEAFIK

DAGGLKGVHF MTKWMLAANG LYPWPRAYIP LSFLLIPSYF

PLHFYHFSTY ARIHFVPMAI TFNRRFSLKN NQIGSLRHLD

EAMSKNPLEW LNIRAFDERT FYSFNLQWKQ LFQWPAYVHQ

LGFEAGKKYM LDRIEEDGTL YSYASATMFM IYSLLAMGIS

KNAPVVKKAV SGIKSLISSC GKEGAHLENS TSTVWDTALI

SYAMQESGVP EQHSSTSSAA DYLLKRQHVK KADWAVSNPQ

AVPGGWGFSH INTNNPDLDD TAAALKAIPF QRRPDAWNRG

LAWLLSMQNK DGGFAAFEKD VDHPLIRNLP LESAAEAAVD

TABLE 6-continued

Tetraprenyl-β-curcumene Cyclase Derived from
Bacillus licheniformis

PSTADLTGRV LHLLGLKGRF TDNHPAVRRA LRWLDHHQKA

DGSWYGRWGV CFIYGTWAAL TGMKAVGVSA NQTSVKKAIS

WLKSIQREDG SWGESCKSCE AKRFVPLHFG TVVQSSWALE

ALLQYERPDD PQIIKGIRFL IDEHESSRER LEYPTGIGLP

NQFYIRYHSY PFVFSLLASS AFIKKAEMRE TY

The tetraprenyl-β-curcumene cyclase encompasses polypeptides which have the amino acid sequences represented by SEQ ID NOs:16 to 18 wherein one or several amino acid residues are substituted, deleted, inserted, or added, and in which a function of producing ambrein from 3-deoxyachilleol A is maintained. The number of amino acid residues which are substituted, deleted, inserted, or added in each of the amino acid sequences represented by SEQ ID NOs:16 to 18 is, specifically, preferably 1 to 20, more preferably 1 to 10, and further preferably 1 to 5.

The tetraprenyl-β-curcumene cyclase encompasses polypeptides which have sequence identity of, for example, 80% or higher, preferably 90% or higher, more preferably 95% or higher, more preferably 97% or higher, more preferably 98% or higher, and particular preferably 99% or higher, to the whole amino acid sequences each represented by SEQ ID NOs:16 to 18, and in which a function of producing ambrein from 3-deoxyachilleol A is maintained.

The tetraprenyl-β-curcumene cyclase may be obtained by genetic engineering based on the amino acid sequence of a tetraprenyl-β-curcumene cyclase which a bacterium of the genus Bacillus produces and/or based on the base sequence of a tetraprenyl-β-curcumene cyclase gene present in a bacterium of the genus Bacillus. Examples of the tetraprenyl-β-curcumene cyclase gene, which is used when a tetraprenyl-β-curcumene cyclase is produced by genetic engineering, include a polynucleotide having the base sequence of the wild-type gene present in a bacterium of the genus Bacillus or a synthesized polynucleotide based on the base sequence of the wild-type gene.

The base sequence of a tetraprenyl-β-curcumene cyclase gene present in a bacterium of the genus Bacillus is known.

As for Bacillus megaterium, the polynucleotide ranging from 2130781 to 2132658 in the genomic sequence of GenBank:CP001982.1 (SEQ ID NO:19, the base sequence starting from the 2130781st base in the genomic sequence of GenBank:CP001982.1) is known.

As for Bacillus subtilis, the polynucleotide (SEQ ID NO:20) described in GenBank:AB618206 is known.

As for Bacillus licheniformis, the polynucleotide ranging from 2209539 to 2211428 in the genomic sequence of GenBank:CP000002.3 (SEQ ID NO:21, the base sequence starting from the 2209539th base in the genomic sequence of GenBank:CP000002.3) is known.

The polynucleotide encoding a tetraprenyl-β-curcumene cyclase encompasses polynucleotides which have the base sequences represented by SEQ ID NOs:19 to 21 wherein one or several bases are substituted, deleted, inserted, or added, and which encode a polypeptide in which a function of producing ambrein from 3-deoxyachilleol A is maintained. The number of bases which are substituted, deleted, inserted, or added in each of the base sequences represented by SEQ ID NOs:19 to 21 is, specifically, preferably 1 to 20, more preferably 1 to 10, and further preferably 1 to 5.

The polynucleotide encoding a tetraprenyl-β-curcumene cyclase encompasses polynucleotides encoding polypeptides which have sequence identity of, for example, 80% or higher, preferably 90% or higher, more preferably 95% or higher, more preferably 97% or higher, more preferably 98% or higher, and particular preferably 99% or higher, to the whole base sequences each represented by SEQ ID NOs:19 to 21, and in which a function of producing ambrein from 3-deoxyachilleol A is maintained.

The polynucleotide encoding a tetraprenyl-β-curcumene cyclase encompasses polynucleotides which hybridize with complementary strands of the base sequences represented by SEQ ID NOs:19 to 21 under stringent conditions, and which encode a polypeptide in which a function of producing ambrein from 3-deoxyachilleol A from squalene. The conditions of hybridization and the stringent conditions are the same as the conditions described for a mutant squalene-hopene cyclase.

Examples of the tetraprenyl-β-curcumene cyclase include a polypeptide which is encoded by the base sequence represented by any one of SEQ ID NOs:19 to 21, a polypeptide which is encoded by the base sequence represented by SEQ ID NO:19 or SEQ ID NO:20, and a polypeptide which is encoded by the base sequence represented by SEQ ID NO:19.

A recombinant vector which is used for expressing a polynucleotide which encodes a tetraprenyl-β-curcumene cyclase is not particularly restricted, and examples thereof include a vector which can be expressed by *Escherichia coli* such as pCold TF, a vector which can be expressed by *Bacillus subtilis* such as pHT01, and a vector which can be expressed by yeast such as pYES2. By introducing a polynucleotide encoding a tetraprenyl-β-curcumene cyclase into such a vector, an enzyme expression vector can be obtained. A host bacterium which is a target for introducing an enzyme expression vector can be appropriately selected according to the type of a recombinant vector to be used, and examples thereof include *Escherichia coli* such as BL21 (DE3), *Bacillus subtilis* such as strain 168, and yeast such as *Saccharomyces cerevisiae*.

The recombinant vector may contain, as needed, a promoter, a splicing signal, a poly(A) addition signal, a selection marker, a ribosome binding sequence (SD sequence), a terminator such as NOS, and/or the like. As the selection marker, a known one such as an antibiotic resistance gene such as a kanamycin resistance gene, an ampicillin resistance gene or a tetracycline resistance gene is used without particular restriction.

The recombinant vector may contain a reporter gene for confirming that an objective gene is introduced. Examples of such a reporter gene include a GUS (β-glucuronidase) gene, a luciferase gene, and a GFP (green fluorescent protein) gene.

A tetraprenyl-β-curcumene cyclase may be produced by culturing a transformant obtained by introducing an enzyme expression vector into a bacterium. A culture medium used for culturing a transformant may be a culture medium which is usually used, and is appropriately selected according to the type of a host. For example, when *Escherichia coli* are cultured, an LB medium or the like is used. An antibiotic may be added to a culture medium according to the type of a selection marker.

A tetraprenyl-β-curcumene cyclase may be obtained by extraction followed by purification from a culture medium which has been obtained by culturing a transformant capable of expressing the enzyme. An extraction liquid containing the enzyme which has been extracted from a transformant in a culture medium may be used as it is. As a method of extracting an enzyme from a transformant, a known method may be applied. A step of extracting an enzyme may comprise, for example, crushing a transformant in an extraction solvent and separating cell contents from crushed pieces of the transformant. The obtained cell contents contain the target tetraprenyl-β-curcumene cyclase.

As the method of crushing a transformant, a known method in which a transformant is crushed and an enzyme liquid can be recovered may be applied, and examples thereof include ultrasonic crushing and glass beads crushing. The conditions of crushing are not particularly restricted as long as the enzyme is not inactivated, such as a condition of not higher than 10° C. and for 15 minutes.

Examples of the method of separating cell contents from crushed pieces of microorganism include sedimentation, centrifugation, filtering separation, and a combination of two or more thereof. Conditions for these separation methods are known to those skilled in the art. The conditions are, for example, from 8,000×g to 15,000×g and from 10 to 20 minutes in the case of centrifugation.

The extraction solvent may be a solvent which is usually used as a solvent for extracting an enzyme, and examples thereof include Tris-HCl buffer and potassium phosphate buffer. The pH of an extraction solvent is, from the viewpoint of enzyme stability, preferably from 3 to 10 and more preferably from 6 to 8.

The extraction solvent may contain a surfactant. Examples of the surfactant include a nonionic surfactant and an ampholytic surfactant. Examples of the nonionic surfactant include: a polyoxyethylene sorbitan fatty acid ester such as poly(oxyethylene)sorbitan monooleate (Tween 80); alkylglucoside such as n-octyl β-D-glucoside; a sucrose fatty acid ester such as sucrose stearate; and a polyglycerol fatty acid ester such as polyglycerol stearate. Examples of the ampholytic surfactant include N,N-dimethyl-N-dodecylglycine betaine which is an alkylbetaine. Besides the above, surfactants generally used in the art such as Triton X-100 (TRITON X-100), polyoxyethylene(20)cetyl ether (BRIJ-58), and nonylphenol ethoxylate (TERGITOL NP-40) can be utilized.

The concentration of a surfactant in an extraction solvent is, from the viewpoint of enzyme stability, preferably from 0.001% by mass to 10% by mass, more preferably from 0.10% by mass to 3.0% by mass, and further preferably from 0.10% by mass to 1.0% by mass.

From the viewpoint of enzyme activity, an extraction solvent preferebly contains a reducing agent such as dithiothreitol or β-mercaptoethanol. The reducing agent is preferably dithiothreitol. The concentration of dithiothreitol in an extraction solvent is preferably from 0.1 mM to 1M and more preferably from 1 mM to 10 mM. In a case that dithiothreitol is present in an extraction solvent, a structure such as a disulfide bond in the enzyme is easily to be retained and enzyme activity is easely to be enhanced.

From the viewpoint of enzyme activity, the extraction solvent preferably contains chelating agent such as ethylenediaminetetraacetic acid (EDTA). The concentration of EDTA in the extraction solvent is preferably from 0.01 mM to 1 M and more preferably from 0.1 mM to 10 mM. In a case that EDTA is present in the extraction solvent, a metal ion which may reduce enzyme activity is chelated, and therefore, enzyme activity is easily to be enhanced.

The extraction solvent may contain, besides the ingredients described above, a known ingredient which can be added to an enzyme extraction solvent.

Tetraprenyl-β-curcumene cyclases may be used singly, or in combination of two or more kinds thereof.

The conditions of a reaction between a tetraprenyl-β-curcumene cyclase and 3-deoxyachilleol A are not particularly restricted as long as the conditions are such that an enzyme reaction can be proceeded. For example, the reaction temperature and the reaction time may be appropriately selected based on the activity of a tetraprenyl-β-curcumene cyclase or the like. From the viewpoint of reaction efficiency, the reaction temperature and the reaction time may be, for example, from 4° C. to 100° C. and from 0.1 hour to 48 hours, and preferably 30° C. to 60° C. and 16 hours to 24 hours. From the viewpoint of reaction efficiency, the pH is, for example, from 3 to 10, and preferably from 6 to 8.

A reaction solvent is not particularly restricted as long as the reaction solvent does not inhibit an enzyme reaction, and a buffer or the like which is usually used can be used. For example, the same solvent as an extraction solvent which is used in a step of extracting an enzyme can be used. An extraction liquid (for example, cell-free extract) containing a tetraprenyl-β-curcumene cyclase may be used as it is as an enzyme liquid in the reaction.

From the viewpoint of reaction efficiency, the concentration ratio between a tetraprenyl-β-curcumene cyclase and 3-deoxyachilleol A which is the substrate thereof in a production reaction of ambrein is preferably from 10 to 10000, more preferably from 100 to 5000, still more preferably from 1000 to 3000, and still further preferably from 1000 to 2000 in terms of the molar concentration ratio (substrate/enzyme) of the substrate to the enzyme.

From the viewpoint of reaction efficiency, the concentration of 3-deoxyachilleol A to be used for an enzyme reaction is preferably from 0.000001% by mass to 0.002% by mass, and more preferably from 0.00001% by mass to 0.0002% by mass with respect to the total mass of the reaction solvent.

A step of reaction between a tetraprenyl-β-curcumene cyclase and 3-deoxyachilleol A may be repeated a plurality of times. This can increase the yield of ambrein. In a case that a plurality of reaction steps are repeated, the purification method may comprise: a step of recharging 3-deoxyachilleol A to be the substrate; a step of recovering and purifying a reaction product in a reaction liquid after inactivating the enzyme by a known method; and the like. In a case that 3-deoxyachilleol A is recharged, a charging point in time and the amount of charging of squalene can be appropriately set according to the concentration of the tetraprenyl-β-curcumene cyclase in the reaction liquid, the amount of the substrate remained in the reaction liquid, or the like.

From the viewpoints of production efficiency of ambrein and simplicity of the production method thereof, the method for producing ambrein in the invention is, in a case that the method comprises a step of producing 3-deoxyachilleol A and an ambrein production step, preferably a method comprising: reacting a tetraprenyl-β-curcumene cyclase derived from a bacterium of the genus *Bacillus* with 3-deoxyachilleol A obtained from a reaction between a mutant squalene-hopene cyclase derived from a bacterum of the genus *Alicyclobacillus* and squalene to produce ambrein. The method for producing ambrein in the invention is more preferably a method comprising: reacting a tetraprenyl-β-curcumene cyclase derived from *Bacillus megaterium* or *Bacillus subtilis* with 3-deoxyachilleol A obtained from a reaction between a mutant squalene-hopene cyclase derived from *Alicyclobacillus acidocaldarius* and squalene to produce ambrein.

[Other Steps]

The method for producing ambrein in the invention may further comprise a purification step which purifies produced ambrein. The purification method of ambrein is not particularly restricted as long as ambrein in a reaction liquid can be taken out, and a purification method which is usually used may be appropriately selected. Specific examples of the purification method include solvent extraction, recrystallization, distillation, column chromatography, and HPLC.

The obtained product can be confirmed to be ambrein by a conventional method using a gas chromatography-mass spectrometer (GC-MS) or a nuclear magnetic resonance apparatus (NMR).

EXAMPLES

In the following, the invention will be described in detail by way of Examples. The invention, however, should not be limited thereto in any way.

Example 1

Ambrein was obtained using squalene as a material by two steps: a step of reacting a mutant squalene-hopene cyclase with squalene; and a step of reacting a tetraprenyl-β-curcumene cyclase with 3-deoxyachilleol A. A reaction scheme of the two steps is illustrated below.

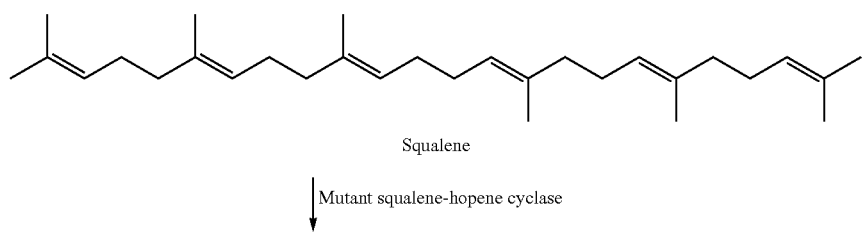

Squalene

Mutant squalene-hopene cyclase

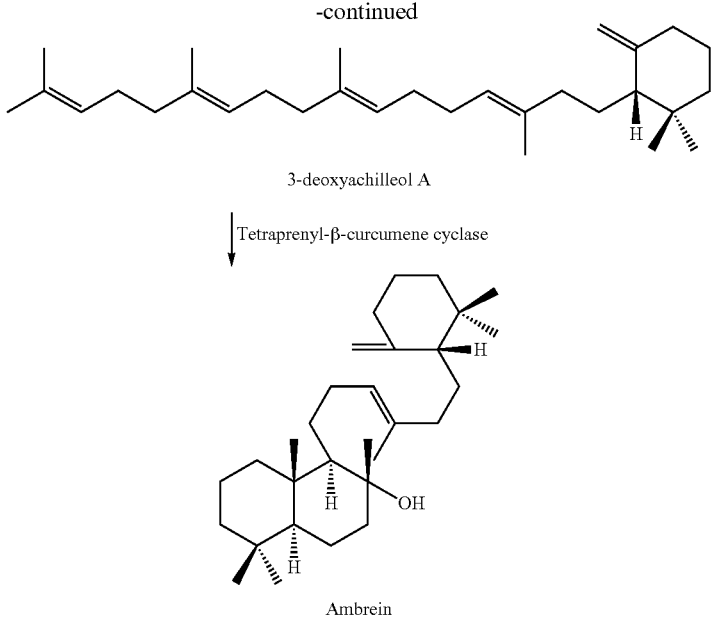

3-deoxyachilleol A

↓ Tetraprenyl-β-curcumene cyclase

Ambrein (1) Synthesis of 3-deoxyachilleol A

Escherichia coli BL21 (DE3) (Biosci. Biotechnol. Biochem., (1999) Vol. 63, pp. 2189-2198) that is transformed with a recombinant vector containing the polynucleotide (SEQ ID NO:9) encoding the mutant squalene-hopene cyclase (SEQ ID NO:2) was prepared. This transformant was inoculated onto an LB medium (6 L) containing ampicillin (50 mg/L) and cultured at 37° C. for 16 hours while shaking. After culturing, bacterial cells were harvested by centrifugation (6,000×g, 10 minutes). The harvested bacterial cells were washed with 50 mM Tris-HCl buffer (pH 8.0), then suspended in 300 mL buffer A [containing 50 mM Tris-HCl buffer (pH 8.0), 1 v/v % Triton X-100], and ultrasonically crushed (4° C., 15 minutes) using UP2005 sonicator (Hielscher Ultrasonics, Teltow, Germany). The crushed sample was centrifuged (12,000×g, 15 minutes), and a supernatant obtained after the centrifugation was designated as "cell-free extract A".

Squalene (50 mg) was mixed with Triton X-100 (1 g) to be solubilized, and a buffer A (5 mL) was added thereto to prepare squalene liquid. The whole of the squalene liquid was added to the cell-free extract A to obtain a reaction liquid, followed by incubation at 60° C. for 16 hours. In the reaction liquid, the mole ratio (substrate/enzyme) of squalene (substrate) to the mutant squalene-hopene cyclase (enzyme) was about 1,000.

After the incubation, ethanol solution containing 15% by mass of potassium hydroxide (KOH/MeOH, 450 mL) was added to the reaction liquid to stop an enzyme reaction. Thereafter, n-hexane (750 mL) was added to the reaction liquid, and the reaction product was extracted three times. The obtained extract was subjected to silica gel column chromatography (solvent: n-hexane) to obtain pure 3-deoxyachilleol A (42.2 mg). The structure of 3-deoxyachilleol A was confirmed by gas chromatography-mass spectrometer (GC-MS) and nuclear magnetic resonance apparatus (NMR).

(2) Synthesis of Ambrein

Escherichia coli BL21 (DE3) (J. Am. Chem. Soc., (2011) Vol. 133, pp. 17540-17543) transformed with a recombinant vector containing the polynucleotide (SEQ ID NO:19) encoding the tetraprenyl-β-curcumene cyclase (SEQ ID NO:16) derived from Bacillus megaterium was prepared. This transformant was inoculated onto an LB medium (18 L) and cultured at 37° C. for 3 hours while shaking. After culturing, 0.1M isopropyl-β-thiogalactopyranoside (IPTG) was added thereto and shaken at 15° C. for 24 hours, and the expression of a tetraprenyl-β-curcumene cyclase was induced.

Thereafter, bacterial cells that was harvested by centrifugation (6,000×g, 10 minutes) were washed with 50 mM Tris-HCl buffer (pH 8.0), then suspended in 540 mL buffer B [containing 50 mM Tris-HCl buffer (pH 7.5), 0.1 v/v % Triton X-100, 2.5 mM dithiothreitol, and 1 mM EDTA], and ultrasonically crushed (4° C., 20 minutes) using UP2005 sonicator (Hielscher Ultrasonics, Teltow, Germany). The crushed sample was centrifuged (12,300×g, 20 minutes), and a supernatant obtained after the centrifugation was designated as "cell-free extract B".

3-deoxyachilleol A (35 mg) obtained in the step (1) was mixed with Triton X-100 (700 mg) to be solubilized, and a buffer B (5 mL) was added thereto to prepare 3-deoxyachilleol A liquid. The whole of the 3-deoxyachilleol A liquid was added to the cell-free extract B (180 mL) to obtain a reaction liquid, followed by incubation at 30° C. for 16 hours. In the reaction liquid, the mole ratio (substrate/enzyme) of 3-deoxyachilleol A (substrate) to a tetraprenyl-β-curcumene cyclase (enzyme) was about 1,000.

After the incubation, ethanol solution containing 15% by mass of potassium hydroxide (KOH/MeOH, 220 mL) was added to the reaction liquid, and a heat treatment was further performed at 70° C. for 30 minutes to stop an enzyme reaction. Thereafter, n-hexane (400 mL) was added to the reaction liquid, and the reaction product was extracted three times. The obtained extract was solubilized by adding Triton X-100 (470 mg) thereto. The solubilized extract was added to buffer B (5 mL), and the buffer was then added to cell-free extract B (180 mL), followed by performing incubation, stopping a reaction, and performing n-hexane extraction in the same manner as above. Subsequently, solubilization of the extract, addition to the cell-free extract B, incubation, stopping of the reaction, and n-hexane extraction were performed once more in the same manner as above.

The obtained extract was subjected to silica gel column chromatography (solvent: n-hexane, n-hexane:ethyl acetate=100:20; volume ratio) to obtain n-hexane:ethyl acetate=100:20 fraction. The obtained fraction was concentrated and subjected to HPLC (solvent: n-hexane:THF=100:20) to obtain pure ambrein (0.4 mg). The structure of ambrein was confirmed by gas chromatography-mass spectrometer (GC-MS) and nuclear magnetic resonance apparatus (NMR). The optical rotation thereof was approximately agreed with the literature value.

Example 2

The step (1) and step (2) were performed in the similar manner as Example 1 except that the tetraprenyl-β-curcumene cyclase was changed from an enzyme derived from Bacillus megaterium to an enzyme derived from Bacillus subtilis to synthesize ambrein. The tetraprenyl-β-curcumene cyclase used in Example 2 is an enzyme encoded by the polynucleotide represented by SEQ ID NO:20 and has the amino acid sequence represented by SEQ ID NO:17.

As a result, in the same manner as Example 1, ambrein was obtainable from squalene via 3-deoxyachilleol A. The yield of the synthesized ambrein was about 10% of the yield in a case (Example 1) in which a tetraprenyl-β-curcumene cyclase derived from Bacillus megaterium was used.

According to the invention, ambrein can be easily produced from 3-deoxyachilleol A by using a tetraprenyl-β-curcumene cyclase.

According to the invention, ambrein can be easily produced from squalene via 3-deoxyachilleol A by using a mutant squalene-hopene cyclase and a tetraprenyl-β-curcumene cyclase.

The disclosure of Japanese Patent Application No. 2013-184143 filed on Sep. 5, 2013 is hereby incorporated by reference in its entirety.

All the references, patent applications and technical standards that are described in the present specification are hereby incorporated by reference to the same extent as if each individual reference, patent application or technical standard is concretely and individually described to be incorporated by reference.

The invention claimed is:

1. A method for producing ambrein, comprising reacting a tetraprenyl-β-curcumene cyclase with 3-deoxyachilleol A to obtain ambrein.

2. The method for producing ambrein according to claim 1, wherein the tetraprenyl-β-curcumene cyclase is derived from a bacterium of the genus *Bacillus*.

3. The method for producing ambrein according to claim 2, wherein the tetraprenyl-β-curcumene cyclase is derived from any one of *Bacillus megaterium, Bacillus subtilis* or *Bacillus licheniformis*.

4. The method for producing ambrein according to claim 2, further comprising reacting a mutant squalene-hopene cyclase-with squalene to obtain 3-deoxyachilleol A, wherein the mutant squalene-hopene cyclase has an amino acid substitution at at least one position selected from the group consisting of position 377, position 420, position 607, and position 612 in the amino acid sequence of SEQ ID NO:1.

5. The method for producing ambrein according to claim 4, wherein the mutant squalene-hopene cyclase has an amino acid sequence of any one of SEQ ID NO:2, SEQ ID NO:3, SEQ ID NO:4, SEQ ID NO:5, SEQ ID NO:6, SEQ ID NO:7, or SEQ ID NO:8.

6. The method for producing ambrein according to claim 1, wherein the tetraprenyl-β-curcumene cyclase is derived from any one of *Bacillus megaterium, Bacillus subtilis* or *Bacillus licheniformis*.

7. The method for producing ambrein according to claim 6, further comprising reacting a mutant squalene-hopene cyclase-with squalene to obtain 3-deoxyachilleol A, wherein the mutant squalene-hopene cyclase has an amino acid substitution at at least one position selected from the group consisting of position 377, position 420, position 607, and position 612 in the amino acid sequence of SEQ ID NO:1.

8. The method for producing ambrein according to claim 7, wherein the mutant squalene-hopene cyclase has an amino acid sequence of any one of SEQ ID NO:2, SEQ ID NO:3, SEQ ID NO:4, SEQ ID NO:5, SEQ ID NO:6, SEQ ID NO:7, or SEQ ID NO:8.

9. The method for producing ambrein according to claim 1, further comprising reacting a mutant squalene-hopene cyclase-with squalene to obtain 3-deoxyachilleol A, wherein the mutant squalene-hopene cyclase has an amino acid substitution at at least one position selected from the group consisting of position 377, position 420, position 607, and position 612 in the amino acid sequence of SEQ ID NO:1.

10. The method for producing ambrein according to claim 9, wherein the mutant squalene-hopene cyclase has an amino acid sequence of any one of SEQ ID NO:2, SEQ ID NO:3, SEQ ID NO:4, SEQ ID NO:5, SEQ ID NO:6, SEQ ID NO:7, or SEQ ID NO:8.

\* \* \* \* \*

SEQUENCE LISTING

```
<160> NUMBER OF SEQ ID NOS: 21

<210> SEQ ID NO 1
<211> LENGTH: 631
<212> TYPE: PRT
<213> ORGANISM: Alicyclobacillus acidocaldarius

<400> SEQUENCE: 1

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
                20                  25                  30

Trp Gly Pro Leu Leu Ser Asn Val Thr Met Glu Ala Glu Tyr Val Leu
            35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Ala
```

-continued

```
            210                 215                 220
Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                    245                 250                 255

Ser Trp Gly Gly Ile Gln Pro Pro Trp Phe Tyr Ala Leu Ile Ala Leu
                260                 265                 270

Lys Ile Leu Asp Met Thr Gln His Pro Ala Phe Ile Lys Gly Trp Glu
            275                 280                 285

Gly Leu Glu Leu Tyr Gly Val Glu Leu Asp Tyr Gly Gly Trp Met Phe
290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                    325                 330                 335

Gly Glu Trp Leu Leu Asp Arg Gln Ile Thr Val Pro Gly Asp Trp Ala
                340                 345                 350

Val Lys Arg Pro Asn Leu Lys Pro Gly Gly Phe Ala Phe Gln Phe Asp
            355                 360                 365

Asn Val Tyr Tyr Pro Asp Val Asp Asp Thr Ala Val Val Trp Ala
370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                    405                 410                 415

Trp Gly Ala Tyr Asp Val Asp Asn Thr Ser Asp Leu Pro Asn His Ile
                420                 425                 430

Pro Phe Cys Asp Phe Gly Glu Val Thr Asp Pro Pro Ser Glu Asp Val
            435                 440                 445

Thr Ala His Val Leu Glu Cys Phe Gly Ser Phe Gly Tyr Asp Asp Ala
450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                    485                 490                 495

Thr Gly Ala Val Val Ser Ala Leu Lys Ala Val Gly Ile Asp Thr Arg
                500                 505                 510

Glu Pro Tyr Ile Gln Lys Ala Leu Asp Trp Val Glu Gln His Gln Asn
            515                 520                 525

Pro Asp Gly Gly Trp Gly Glu Asp Cys Arg Ser Tyr Glu Asp Pro Ala
530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                    565                 570                 575

Gly Val Gln Tyr Leu Val Glu Thr Gln Arg Pro Asp Gly Gly Trp Asp
                580                 585                 590

Glu Pro Tyr Tyr Thr Gly Thr Gly Phe Pro Gly Asp Phe Tyr Leu Gly
            595                 600                 605

Tyr Thr Met Tyr Arg His Val Phe Pro Thr Leu Ala Leu Gly Arg Tyr
610                 615                 620

Lys Gln Ala Ile Glu Arg Arg
625                 630
```

<210> SEQ ID NO 2
<211> LENGTH: 631
<212> TYPE: PRT
<213> ORGANISM: Artificial Sequence
<220> FEATURE:
<223> OTHER INFORMATION: mutant squalene-hopene cyclase_D377C

<400> SEQUENCE: 2

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Ala
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365
```

```
Asn Val Tyr Tyr Pro Asp Val Asp Cys Thr Ala Val Val Trp Ala
        370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
                420                 425                 430

Pro Phe Cys Asp Phe Gly Glu Val Thr Asp Pro Pro Ser Glu Asp Val
                435                 440                 445

Thr Ala His Val Leu Glu Cys Phe Gly Ser Phe Gly Tyr Asp Asp Ala
            450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
            515                 520                 525

Pro Asp Gly Gly Trp Gly Glu Asp Cys Arg Ser Tyr Glu Asp Pro Ala
        530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
            595                 600                 605

Tyr Thr Met Tyr Arg His Val Phe Pro Thr Leu Ala Leu Gly Arg Tyr
        610                 615                 620

Lys Gln Ala Ile Glu Arg Arg
625                 630

<210> SEQ ID NO 3
<211> LENGTH: 631
<212> TYPE: PRT
<213> ORGANISM: Artificial Sequence
<220> FEATURE:
<223> OTHER INFORMATION: mutant squalene-hopene cyclase_D377N

<400> SEQUENCE: 3

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
                20                  25                  30

Trp Gly Pro Leu Leu Ser Asn Val Thr Met Glu Ala Glu Tyr Val Leu
            35                  40                  45

Leu Cys His Ile Leu Asp Arg Val Asp Arg Asp Arg Met Glu Lys Ile
        50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95
```

```
Ala Leu Lys Tyr Ile Gly Met Ser Arg Asp Glu Pro Met Gln Lys
            100                 105                 110

Ala Leu Arg Phe Ile Gln Ser Gln Gly Gly Ile Glu Ser Arg Val
            115                 120                 125

Phe Thr Arg Met Trp Leu Ala Leu Val Gly Glu Tyr Pro Trp Glu Lys
130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
                180                 185                 190

Ala Arg Val Pro Glu Leu Tyr Glu Thr Asp Val Pro Pro Arg Arg Arg
                195                 200                 205

Gly Ala Lys Gly Gly Gly Gly Trp Ile Phe Asp Ala Leu Asp Arg Ala
                210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
                260                 265                 270

Lys Ile Leu Asp Met Thr Gln His Pro Ala Phe Ile Lys Gly Trp Glu
                275                 280                 285

Gly Leu Glu Leu Tyr Gly Val Glu Leu Asp Tyr Gly Gly Trp Met Phe
                290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
                340                 345                 350

Val Lys Arg Pro Asn Leu Lys Pro Gly Gly Phe Ala Phe Gln Phe Asp
                355                 360                 365

Asn Val Tyr Tyr Pro Asp Val Asp Asn Thr Ala Val Val Val Trp Ala
                370                 375                 380

Leu Asn Thr Leu Arg Leu Pro Asp Glu Arg Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
                420                 425                 430

Pro Phe Cys Asp Phe Gly Glu Val Thr Asp Pro Pro Ser Glu Asp Val
                435                 440                 445

Thr Ala His Val Leu Glu Cys Phe Gly Ser Phe Gly Tyr Asp Asp Ala
                450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
                500                 505                 510
```

-continued

```
Glu Pro Tyr Ile Gln Lys Ala Leu Asp Trp Val Glu His Gln Asn
        515                 520                 525

Pro Asp Gly Gly Trp Gly Glu Asp Cys Arg Ser Tyr Glu Asp Pro Ala
530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630
```

<210> SEQ ID NO 4
<211> LENGTH: 631
<212> TYPE: PRT
<213> ORGANISM: Artificial Sequence
<220> FEATURE:
<223> OTHER INFORMATION: mutant squalene-hopene cyclase_Y420H

<400> SEQUENCE: 4

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
                20                  25                  30

Trp Gly Pro Leu Leu Ser Asn Val Thr Met Glu Ala Glu Tyr Val Leu
            35                  40                  45

Leu Cys His Ile Leu Asp Arg Val Asp Arg Asp Arg Met Glu Lys Ile
        50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Ala
    210                 215                 220

Leu His Gly Tyr Gln Lys Leu Ser Val His Pro Phe Arg Arg Ala Ala
225                 230                 235                 240
```

```
Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala His Asp Val Asp Asn Thr Ser Asp Leu Pro Asn His Ile
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630

<210> SEQ ID NO 5
<211> LENGTH: 631
<212> TYPE: PRT
```

<213> ORGANISM: Artificial Sequence
<220> FEATURE:
<223> OTHER INFORMATION: mutant squalene-hopene cyclase_Y420W

<400> SEQUENCE: 5

```
Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Ala
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
        275                 280                 285

Gly Leu Glu Leu Tyr Gly Val Glu Leu Asp Tyr Gly Gly Trp Met Phe
    290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
        355                 360                 365

Asn Val Tyr Tyr Pro Asp Val Asp Asp Thr Ala Val Val Val Trp Ala
    370                 375                 380

Leu Asn Thr Leu Arg Leu Pro Asp Glu Arg Arg Arg Arg Asp Ala Met
```

-continued

```
                385                 390                 395                 400
        Thr Lys Gly Phe Arg Trp Ile Val Gly Met Gln Ser Ser Asn Gly Gly
                        405                 410                 415

Trp Gly Ala Trp Asp Val Asp Asn Thr Ser Asp Leu Pro Asn His Ile
                        420                 425                 430

Pro Phe Cys Asp Phe Gly Glu Val Thr Asp Pro Pro Ser Glu Asp Val
                        435                 440                 445

Thr Ala His Val Leu Glu Cys Phe Gly Ser Phe Gly Tyr Asp Asp Ala
                        450                 455                 460

Trp Lys Val Ile Arg Arg Ala Val Glu Tyr Leu Lys Arg Glu Gln Lys
        465                 470                 475                 480

Pro Asp Gly Ser Trp Phe Gly Arg Trp Gly Val Asn Tyr Leu Tyr Gly
                        485                 490                 495

Thr Gly Ala Val Val Ser Ala Leu Lys Ala Val Gly Ile Asp Thr Arg
                        500                 505                 510

Glu Pro Tyr Ile Gln Lys Ala Leu Asp Trp Val Glu Gln His Gln Asn
                        515                 520                 525

Pro Asp Gly Gly Trp Gly Glu Asp Cys Arg Ser Tyr Glu Asp Pro Ala
                        530                 535                 540

Tyr Ala Gly Lys Gly Ala Ser Thr Pro Ser Gln Thr Ala Trp Ala Leu
        545                 550                 555                 560

Met Ala Leu Ile Ala Gly Gly Arg Ala Glu Ser Glu Ala Ala Arg Arg
                        565                 570                 575

Gly Val Gln Tyr Leu Val Glu Thr Gln Arg Pro Asp Gly Gly Trp Asp
                        580                 585                 590

Glu Pro Tyr Tyr Thr Gly Thr Gly Phe Pro Gly Asp Phe Tyr Leu Gly
                        595                 600                 605

Tyr Thr Met Tyr Arg His Val Phe Pro Thr Leu Ala Leu Gly Arg Tyr
                        610                 615                 620

Lys Gln Ala Ile Glu Arg Arg
        625                 630

<210> SEQ ID NO 6
<211> LENGTH: 631
<212> TYPE: PRT
<213> ORGANISM: Artificial Sequence
<220> FEATURE:
<223> OTHER INFORMATION: mutant squalene-hopene cyclase_L607F

<400> SEQUENCE: 6

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
                20                  25                  30

Trp Gly Pro Leu Leu Ser Asn Val Thr Met Glu Ala Glu Tyr Val Leu
                35                  40                  45

Leu Cys His Ile Leu Asp Arg Val Asp Arg Asp Met Glu Lys Ile
                50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                        85                  90                  95

Ala Leu Lys Tyr Ile Gly Met Ser Arg Asp Glu Glu Pro Met Gln Lys
                100                 105                 110

Ala Leu Arg Phe Ile Gln Ser Gln Gly Gly Ile Glu Ser Ser Arg Val
```

```
            115                 120                 125
Phe Thr Arg Met Trp Leu Ala Leu Val Gly Glu Tyr Pro Trp Glu Lys
130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                    165                 170                 175

Leu Ser Ile Val Met Ser Arg Gln Pro Val Phe Pro Leu Pro Glu Arg
                    180                 185                 190

Ala Arg Val Pro Glu Leu Tyr Glu Thr Asp Val Pro Arg Arg Arg
                    195                 200                 205

Gly Ala Lys Gly Gly Gly Trp Ile Phe Asp Ala Leu Asp Arg Ala
210                 215                 220

Leu His Gly Tyr Gln Lys Leu Ser Val His Pro Phe Arg Ala Ala
225                 230                 235                 240

Glu Ile Arg Ala Leu Asp Trp Leu Leu Glu Arg Gln Ala Gly Asp Gly
                    245                 250                 255

Ser Trp Gly Gly Ile Gln Pro Pro Trp Phe Tyr Ala Leu Ile Ala Leu
                    260                 265                 270

Lys Ile Leu Asp Met Thr Gln His Pro Ala Phe Ile Lys Gly Trp Glu
                    275                 280                 285

Gly Leu Glu Leu Tyr Gly Val Glu Leu Asp Tyr Gly Gly Trp Met Phe
290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                    325                 330                 335

Gly Glu Trp Leu Leu Asp Arg Gln Ile Thr Val Pro Gly Asp Trp Ala
                    340                 345                 350

Val Lys Arg Pro Asn Leu Lys Pro Gly Gly Phe Ala Phe Gln Phe Asp
                    355                 360                 365

Asn Val Tyr Tyr Pro Asp Val Asp Asp Thr Ala Val Val Trp Ala
370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                    405                 410                 415

Trp Gly Ala Tyr Asp Val Asp Asn Thr Ser Asp Leu Pro Asn His Ile
                    420                 425                 430

Pro Phe Cys Asp Phe Gly Glu Val Thr Asp Pro Pro Ser Glu Asp Val
                    435                 440                 445

Thr Ala His Val Leu Glu Cys Phe Gly Ser Phe Gly Tyr Asp Asp Ala
                    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                    485                 490                 495

Thr Gly Ala Val Val Ser Ala Leu Lys Ala Val Gly Ile Asp Thr Arg
                    500                 505                 510

Glu Pro Tyr Ile Gln Lys Ala Leu Asp Trp Val Glu Gln His Gln Asn
                    515                 520                 525

Pro Asp Gly Gly Trp Gly Glu Asp Cys Arg Ser Tyr Glu Asp Pro Ala
530                 535                 540
```

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Phe Gly
        595                 600                 605

Tyr Thr Met Tyr Arg His Val Phe Pro Thr Leu Ala Leu Gly Arg Tyr
    610                 615                 620

Lys Gln Ala Ile Glu Arg Arg
625                 630

<210> SEQ ID NO 7
<211> LENGTH: 631
<212> TYPE: PRT
<213> ORGANISM: Artificial Sequence
<220> FEATURE:
<223> OTHER INFORMATION: mutant squalene-hopene cyclase_L607W

<400> SEQUENCE: 7

Met Ala Glu Gln Leu Val Glu Ala Pro Ala Tyr Ala Arg Thr Leu Asp
1               5                   10                  15

Arg Ala Val Glu Tyr Leu Leu Ser Cys Gln Lys Asp Glu Gly Tyr Trp
            20                  25                  30

Trp Gly Pro Leu Leu Ser Asn Val Thr Met Glu Ala Glu Tyr Val Leu
        35                  40                  45

Leu Cys His Ile Leu Asp Arg Val Asp Arg Asp Arg Met Glu Lys Ile
    50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
            100                 105                 110

Ala Leu Arg Phe Ile Gln Ser Gln Gly Gly Ile Glu Ser Ser Arg Val
        115                 120                 125

Phe Thr Arg Met Trp Leu Ala Leu Val Gly Glu Tyr Pro Trp Glu Lys
    130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
            180                 185                 190

Ala Arg Val Pro Glu Leu Tyr Glu Thr Asp Val Pro Pro Arg Arg Arg
        195                 200                 205

Gly Ala Lys Gly Gly Gly Gly Trp Ile Phe Asp Ala Leu Asp Arg Ala
    210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

```
Lys Ile Leu Asp Met Thr Gln His Pro Ala Phe Ile Lys Gly Trp Glu
            275                 280                 285

Gly Leu Glu Leu Tyr Gly Val Glu Leu Asp Tyr Gly Gly Trp Met Phe
290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
            355                 360                 365

Asn Val Tyr Tyr Pro Asp Val Asp Asp Thr Ala Val Val Trp Ala
            370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415

Trp Gly Ala Tyr Asp Val Asp Asn Thr Ser Asp Leu Pro Asn His Ile
            420                 425                 430

Pro Phe Cys Asp Phe Gly Glu Val Thr Asp Pro Pro Ser Glu Asp Val
            435                 440                 445

Thr Ala His Val Leu Glu Cys Phe Gly Ser Phe Gly Tyr Asp Asp Ala
            450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu Gln His Gln Asn
            515                 520                 525

Pro Asp Gly Gly Trp Gly Glu Asp Cys Arg Ser Tyr Glu Asp Pro Ala
            530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Trp Gly
            595                 600                 605

Tyr Thr Met Tyr Arg His Val Phe Pro Thr Leu Ala Leu Gly Arg Tyr
610                 615                 620

Lys Gln Ala Ile Glu Arg Arg
625                 630
```

<210> SEQ ID NO 8
<211> LENGTH: 631
<212> TYPE: PRT
<213> ORGANISM: Artificial Sequence
<220> FEATURE:
<223> OTHER INFORMATION: mutant squalene-hopene cyclase_Y612A

<400> SEQUENCE: 8

```
Met Ala Glu Gln Leu Val Glu Ala Pro Ala Arg Thr Leu Asp
1               5                   10                  15

Arg Ala Val Glu Tyr Leu Leu Ser Cys Gln Lys Asp Glu Gly Tyr Trp
                20                  25                  30

Trp Gly Pro Leu Leu Ser Asn Val Thr Met Glu Ala Glu Tyr Val Leu
                35                  40                  45

Leu Cys His Ile Leu Asp Arg Val Asp Arg Asp Arg Met Glu Lys Ile
            50                  55                  60

Arg Arg Tyr Leu Leu His Glu Gln Arg Glu Asp Gly Thr Trp Ala Leu
65                  70                  75                  80

Tyr Pro Gly Gly Pro Pro Asp Leu Asp Thr Thr Ile Glu Ala Tyr Val
                85                  90                  95

Ala Leu Lys Tyr Ile Gly Met Ser Arg Asp Glu Glu Pro Met Gln Lys
                100                 105                 110

Ala Leu Arg Phe Ile Gln Ser Gln Gly Gly Ile Glu Ser Ser Arg Val
                115                 120                 125

Phe Thr Arg Met Trp Leu Ala Leu Val Gly Glu Tyr Pro Trp Glu Lys
            130                 135                 140

Val Pro Met Val Pro Pro Glu Ile Met Phe Leu Gly Lys Arg Met Pro
145                 150                 155                 160

Leu Asn Ile Tyr Glu Phe Gly Ser Trp Ala Arg Ala Thr Val Val Ala
                165                 170                 175

Leu Ser Ile Val Met Ser Arg Gln Pro Val Phe Pro Leu Pro Glu Arg
                180                 185                 190

Ala Arg Val Pro Glu Leu Tyr Glu Thr Asp Val Pro Arg Arg Arg
                195                 200                 205

Gly Ala Lys Gly Gly Gly Gly Trp Ile Phe Asp Ala Leu Asp Arg Ala
            210                 215                 220

Leu His Gly Tyr Gln Lys Leu Ser Val His Pro Phe Arg Arg Ala Ala
225                 230                 235                 240

Glu Ile Arg Ala Leu Asp Trp Leu Leu Glu Arg Gln Ala Gly Asp Gly
                245                 250                 255

Ser Trp Gly Gly Ile Gln Pro Pro Trp Phe Tyr Ala Leu Ile Ala Leu
            260                 265                 270

Lys Ile Leu Asp Met Thr Gln His Pro Ala Phe Ile Lys Gly Trp Glu
            275                 280                 285

Gly Leu Glu Leu Tyr Gly Val Glu Leu Asp Tyr Gly Gly Trp Met Phe
            290                 295                 300

Gln Ala Ser Ile Ser Pro Val Trp Asp Thr Gly Leu Ala Val Leu Ala
305                 310                 315                 320

Leu Arg Ala Ala Gly Leu Pro Ala Asp His Asp Arg Leu Val Lys Ala
                325                 330                 335

Gly Glu Trp Leu Leu Asp Arg Gln Ile Thr Val Pro Gly Asp Trp Ala
            340                 345                 350

Val Lys Arg Pro Asn Leu Lys Pro Gly Gly Phe Ala Phe Gln Phe Asp
                355                 360                 365

Asn Val Tyr Tyr Pro Asp Val Asp Asp Thr Ala Val Val Val Trp Ala
            370                 375                 380

Leu Asn Thr Leu Arg Leu Pro Asp Glu Arg Arg Arg Asp Ala Met
385                 390                 395                 400

Thr Lys Gly Phe Arg Trp Ile Val Gly Met Gln Ser Ser Asn Gly Gly
                405                 410                 415
```

```
Trp Gly Ala Tyr Asp Val Asp Asn Thr Ser Asp Leu Pro Asn His Ile
            420                 425                 430

Pro Phe Cys Asp Phe Gly Glu Val Thr Asp Pro Pro Ser Glu Asp Val
        435                 440                 445

Thr Ala His Val Leu Glu Cys Phe Gly Ser Phe Gly Tyr Asp Asp Ala
    450                 455                 460

Trp Lys Val Ile Arg Arg Ala Val Glu Tyr Leu Lys Arg Glu Gln Lys
465                 470                 475                 480

Pro Asp Gly Ser Trp Phe Gly Arg Trp Gly Val Asn Tyr Leu Tyr Gly
                485                 490                 495

Thr Gly Ala Val Val Ser Ala Leu Lys Ala Val Gly Ile Asp Thr Arg
            500                 505                 510

Glu Pro Tyr Ile Gln Lys Ala Leu Asp Trp Val Glu His Gln Asn
        515                 520                 525

Pro Asp Gly Gly Trp Gly Glu Asp Cys Arg Ser Tyr Glu Asp Pro Ala
    530                 535                 540

Tyr Ala Gly Lys Gly Ala Ser Thr Pro Ser Gln Thr Ala Trp Ala Leu
545                 550                 555                 560

Met Ala Leu Ile Ala Gly Gly Arg Ala Glu Ser Glu Ala Ala Arg Arg
                565                 570                 575

Gly Val Gln Tyr Leu Val Glu Thr Gln Arg Pro Asp Gly Gly Trp Asp
            580                 585                 590

Glu Pro Tyr Tyr Thr Gly Thr Gly Phe Pro Gly Asp Phe Tyr Leu Gly
        595                 600                 605

Tyr Thr Met Ala Arg His Val Phe Pro Thr Leu Ala Leu Gly Arg Tyr
    610                 615                 620

Lys Gln Ala Ile Glu Arg Arg
625                 630

<210> SEQ ID NO 9
<211> LENGTH: 1896
<212> TYPE: DNA
<213> ORGANISM: Artificial Sequence
<220> FEATURE:
<223> OTHER INFORMATION: mutant squalene-hopene
      cyclase_Polynucleotide_D377C

<400> SEQUENCE: 9
atggctgagc agttggtgga agcgccggcc tacgcgcgga cgctggatcg cgcggtggag      60
tatctcctct cctgccaaaa ggacgaaggc tactggtggg gccgcttct gagcaacgtc     120 acgatggaag cggagtacgt cctcttgtgc acattctcg atcgcgtcga tcgggatcgc     180
atggagaaga tccggcggta cctgttgcac gagcagcgcg aggacggcac gtgggccctg     240
tacccgggtg gccgccgga cctcgacacg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggatgtggc tggcgctggt gggagaatat     420
ccgtgggaga aggtgcccat ggtcccgccg gagatcatgt tcctcggcaa gcgcatgccg     480
ctcaacatct acgagtttgg ctcgtgggct cgggcgaccg tcgtggcgct ctcgattgtg     540
atgagccgcc agccggtgtt cccgctgccc gagcgggcgc gcgtgcccga gctgtacgag     600
accgacgtgc ctccgcgccg gcgcggcgcc aagggagggg gtgggtggat cttcgacgcg     660
ctcgaccggg cgctgcacgg gtatcagaag ctgtcggtgc acccgttccg ccgcgcggcc     720
gagatccgcg ccttggactg gttgctcgag cgccaggccg agacggcag ctggggcggg     780
```

```
attcagccgc cttggttta cgcgctcatc gcgctcaaga ttctcgacat gacgcagcat      840
ccggcgttca tcaagggctg ggaaggtcta gagctgtacg gcgtggagct ggattacgga      900
ggatggatgt ttcaggcttc catctcgccg gtgtgggaca cgggcctcgc cgtgctcgcg      960
ctgcgcgctg cggggcttcc ggccgatcac gaccgcttgg tcaaggcggg cgagtggctg     1020
ttggaccggc agatcacggt tccgggcgac tgggcggtga agcgcccgaa cctcaagccg     1080
ggcgggttcg cgttccagtt cgacaacgtg tactacccgg acgtggactg cacggccgtc     1140
gtggtgtggg cgctcaacac cctgcgcttg ccggacgagc gccgcaggcg ggacgccatg     1200
acgaagggat ccgctggat tgtcggcatg cagagctcga acggcggttg gggcgcctac      1260
gacgtcgaca cacgagcga tctcccgaac cacatcccgt tctgcgactt cggcgaagtg      1320
accgatccgc cgtcagagga cgtcaccgcc cacgtgctcg agtgtttcgg cagcttcggg     1380
tacgatgacg cctggaaggt catccggcgc gcggtggaat atctcaagcg ggagcagaag     1440
ccggacggca gctggttcgg tcgttgtggg gtcaattacc tctacggcac gggcgcggtg     1500
gtgtcggcgc tgaaggcggt cgggatcgac acgcgcgagc cgtacattca aaaggcgctc     1560
gactgggtcg agcagcatca gaacccggac ggcggctggg cgaggactg ccgctcgtac      1620
gaggatccgg cgtacgcggg taaggcgcg agcacccgt cgcagacggc ctgggcgctg       1680
atggcgctca tcgcgggcgg cagggcggag tccgaggccg cgcgccgcgg cgtgcaatac     1740
ctcgtggaga cgcagcgccc ggacggcggc tgggatgagc cgtactacac cggcacgggc     1800
ttcccagggg atttctacct cggctacacc atgtaccgcc acgtgtttcc gacgctcgcg     1860
ctcggccgct acaagcaagc catcgagcgc aggtga                               1896
```

<210> SEQ ID NO 10
<211> LENGTH: 1896
<212> TYPE: DNA
<213> ORGANISM: Artificial Sequence
<220> FEATURE:
<223> OTHER INFORMATION: mutant squalene-hopene
      cyclase_Polynucleotide_D377N

<400> SEQUENCE: 10

```
atggctgagc agttggtgga agcgccggcc tacgcgcgga cgctggatcg cgcggtggag       60
tatctcctct cctgccaaaa ggacgaaggc tactggtggg ggccgcttct gagcaacgtc      120
acgatggaag cggagtacgt cctcttgtgc cacattctcg atcgcgtcga tcggatcgc       180
atggagaaga tccggcggta cctgttgcac gagcagcgcg aggacggcac gtgggccctg      240
tacccgggtg ggccgccgga cctcgacacg accatcgagg cgtacgtcgc gctcaagtat      300
atcggcatgt cgcgcgacga ggagccgatg cagaaggcgc tccggttcat tcagagccag      360
ggcgggatcg agtcgtcgcg cgtgttcacg cggatgtggc tggcgctggt gggagaatat      420
ccgtgggaga aggtgcccat ggtcccgccg gagatcatgt tcctcggcaa gcgcatgccg      480
ctcaacatct cgagtttgg ctcgtgggct cgggcgaccg tcgtggcgct tcgattgtg        540
atgagccgcc agccggtgtt cccgctgccc gagcgggcgc gcgtgcccga gctgtacgag      600
accgacgtgc ctccgcgccg gcgcggcgcc aagggagggg gtgggtggat cttcgacgcg      660
ctcgaccggg cgctgcacgg gtatcagaag ctgtcggtgc acccgttccg ccgcgcggcc      720
gagatccgcg ccttggactg gttgctcgag cgccaggccg agacggcag ctggggcggg      780
attcagccgc cttggttta cgcgctcatc gcgctcaaga ttctcgacat gacgcagcat      840
ccggcgttca tcaagggctg ggaaggtcta gagctgtacg gcgtggagct ggattacgga      900
```

```
ggatggatgt tcaggcttc catctcgccg gtgtgggaca cgggcctcgc cgtgctcgcg      960
ctgcgcgctg cggggcttcc ggccgatcac gaccgcttgg tcaaggcggg cgagtggctg     1020
ttggaccggc agatcacggt tccgggcgac tgggcggtga agcgcccgaa cctcaagccg     1080
ggcgggttcg cgttccagtt cgacaacgtg tactacccgg acgtggacaa cacggccgtc     1140
gtggtgtggg cgctcaacac cctgcgcttg ccggacgagc gccgcaggcg ggacgccatg     1200
acgaagggat ccgctggat tgtcggcatg cagagctcga acggcggttg gggcgcctac      1260
gacgtcgaca acacgagcga tctcccgaac cacatcccgt tctgcgactt cggcgaagtg     1320
accgatccgc cgtcagagga cgtcaccgcc cacgtgctcg agtgtttcgg cagcttcggg     1380
tacgatgacg cctggaaggt catccggcgc gcggtggaat atctcaagcg ggagcagaag     1440
ccggacggca gctggttcgg tcgttggggc gtcaattacc tctacggcac gggcgcggtg     1500
gtgtcggcgc tgaaggcggt cgggatcgac acgcgcgagc cgtacattca aaaggcgctc     1560
gactgggtcg agcagcatca gaacccggac ggcggctggg gcgaggactg ccgctcgtac     1620
gaggatccgg cgtacgcggg taaggcgcg agcaccccgt cgcagacggc ctgggcgctg      1680
atggcgctca tcgcgggcgg cagggcggag tccgaggccg cgcgccgcgg cgtgcaatac     1740
ctcgtggaga cgcagcgccc ggacggcggc tgggatgagc cgtactacac cggcacgggc     1800
ttcccagggg atttctacct cggctacacc atgtaccgcc acgtgtttcc gacgctcgcg     1860
ctcggccgct acaagcaagc catcgagcgc aggtga                              1896
```

<210> SEQ ID NO 11
<211> LENGTH: 1896
<212> TYPE: DNA
<213> ORGANISM: Artificial Sequence
<220> FEATURE:
<223> OTHER INFORMATION: mutant squalene-hopene cyclase_Polynucleotide_Y420H

<400> SEQUENCE: 11

```
atggctgagc agttggtgga agcgccggcc tacgcgcgga cgctggatcg cgcggtggag      60
tatctcctct cctgccaaaa ggacgaaggc tactggtggg ggccgcttct gagcaacgtc     120
acgatggaag cggagtacgt cctcttgtgc cacattctcg atcgcgtcga tcgggatcgc     180
atggagaaga tccggcggta cctgttgcac gagcagcgcg aggacggcac gtgggccctg     240
tacccgggtg ggccgccgga cctcgacacg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggatgtggc tggcgctggt gggagaatat     420
ccgtgggaga aggtgcccat ggtcccgccg gagatcatgt tcctcggcaa cgcatgccg      480
ctcaacatct cgagtttggg ctcgtgggct cgggcgaccg tcgtggcgct tcgattgtg      540
atgagccgcc agccggtgtt cccgctgccc gagcgggcgc gcgtgcccga gctgtacgag     600
accgacgtgc tccgcgccg gcgcggcgcc aaggagggg gtgggtggat cttcgacgcg      660
ctcgaccggg cgctgcacgg gtatcagaag ctgtcggtgc acccgttccg ccgcgcggcc     720
gagatccgcg ccttgactg gttgctcgag cgccaggccg agacggcag ctggggcggg      780
attcagccgc cttggttttta cgcgctcatc gcgctcaaga ttctcgacat gacgcagcat     840
ccggcgttca tcaagggctg ggaaggtcta gagctgtacg gcgtggagct ggattacgga     900
ggatggatgt ttcaggcttc catctcgccg gtgtgggaca cgggcctcgc cgtgctcgcg     960
ctgcgcgctg cggggcttcc ggccgatcac gaccgcttgg tcaaggcggg cgagtggctg    1020
```

```
ttggaccggc agatcacggt tccgggcgac tgggcggtga agcgcccgaa cctcaagccg   1080
ggcgggttcg cgttccagtt cgacaacgtg tactacccgg acgtggacga cacggccgtc   1140
gtggtgtggg cgctcaacac cctgcgcttg ccggacgagc gccgcaggcg ggacgccatg   1200
acgaagggat tccgctggat tgtcggcatg cagagctcga acggcggttg gggcgcccac   1260
gacgtcgaca acacgagcga tctcccgaac cacatcccgt tctgcgactt cggcgaagtg   1320
accgatccgc cgtcagagga cgtcaccgcc cacgtgctcg agtgtttcgg cagcttcggg   1380
tacgatgacg cctggaaggt catccggcgc gcggtggaat atctcaagcg ggagcagaag   1440
ccggacggca gctggttcgg tcgttggggc gtcaattacc tctacggcac gggcgcggtg   1500
gtgtcggcgc tgaaggcggt cgggatcgac acgcgcgagc cgtacattca aaaggcgctc   1560
gactgggtcg agcagcatca gaacccggac ggcggctggg gcgaggactg ccgctcgtac   1620
gaggatccgg cgtacgcggg taagggcgcg agcacccccgt cgcagacggc ctgggcgctg   1680
atggcgctca tcgcgggcgg cagggcggag tccgaggccg cgcgccgcgg cgtgcaatac   1740
ctcgtggaga cgcagcgccc ggacggcggc tgggatgagc cgtactacac cggcacgggc   1800
ttcccagggg atttctacct cggctacacc atgtaccgcc acgtgtttcc gacgctcgcg   1860
ctcggccgct acaagcaagc catcgagcgc aggtga                             1896
```

<210> SEQ ID NO 12
<211> LENGTH: 1896
<212> TYPE: DNA
<213> ORGANISM: Artificial Sequence
<220> FEATURE:
<223> OTHER INFORMATION: mutant squalene-hopene
      cyclase_Polynucleotide_Y420W

<400> SEQUENCE: 12

```
atggctgagc agttggtgga agcgccggcc tacgcgcgga cgctggatcg cgcggtggag     60
tatctcctct cctgccaaaa ggacgaaggc tactggtggg ggccgcttct gagcaacgtc    120
acgatggaag cggagtacgt cctcttgtgc cacattctcg atcgcgtcga tcgggatcgc    180
atggagaaga tccggcggta cctgttgcac gagcagcgcg aggacggcac gtgggccctg    240
tacccgggtg ggccgccgga cctcgacacg accatcgagg cgtacgtcgc gctcaagtat    300
atcggcatgt cgcgcgacga ggagccgatg cagaaggcgc tccggttcat tcagagccag    360
ggcgggatcg agtcgtcgcg cgtgttcacg cggatgtggc tggcgctggt gggagaatat    420
ccgtgggaga aggtgcccat ggtcccgccg gagatcatgt tcctcggcaa gcgcatgccg    480
ctcaacatct cgagtttggg ctcgtgggct cgggcgaccg tcgtggcgct ctcgattgtg    540
atgagccgcc agccggtgtt cccgctgccc gagcgggcgc gcgtgcccga gctgtacgag    600
accgacgtgc tccgcgccg gcgcggcgcc aagggagggg gtgggtggat cttcgacgcg    660
ctcgaccggg cgctgcacgg gtatcagaag ctgtcggtgc acccgttccg ccgcgcggcc    720
gagatcgccg ccttggactg gttgctcgag cgccaggccg gagacggcag ctggggcggg    780
attcagccgc cttggttta cgcgctcatc gcgctcaaga ttctcgacat gacgcagcat    840
ccggcgttca tcaagggctg gaaggtctta gagctgtacg gcgtggagct ggattacgga    900
ggatggatgt tcaggcttc catctcgccg gtgtgggaca cgggcctcgc cgtgctcgcg    960
ctgcgcgctg cggggcttcc ggccgatcac gaccgcttgg tcaaggcggg cgagtggctg   1020
ttggaccggc agatcacggt tccgggcgac tgggcggtga agcgcccgaa cctcaagccg   1080
ggcgggttcg cgttccagtt cgacaacgtg tactacccgg acgtggacga cacggccgtc   1140
```

```
gtggtgtggg cgctcaacac cctgcgcttg ccggacgagc gccgcaggcg ggacgccatg    1200
acgaagggat tccgctggat tgtcggcatg cagagctcga acggcggttg gggcgcctgg    1260
gacgtcgaca acacgagcga tctcccgaac cacatcccgt tctgcgactt cggcgaagtg    1320
accgatccgc cgtcagagga cgtcaccgcc cacgtgctcg agtgtttcgg cagcttcggg    1380
tacgatgacg cctggaaggt catccggcgc gcggtggaat atctcaagcg ggagcagaag    1440
ccggacggca gctggttcgg tcgttggggc gtcaattacc tctacggcac gggcgcggtg    1500
gtgtcggcgc tgaaggcggt cgggatcgac acgcgcgagc cgtacattca aaaggcgctc    1560
gactgggtcg agcagcatca gaacccggac ggcggctggg gcgaggactg ccgctcgtac    1620
gaggatccgg cgtacgcggg taagggcgcg agcaccccgt cgcagacggc ctgggcgctg    1680
atggcgctca tcgcgggcgg cagggcggag tccgaggccg cgcgccgcgg cgtgcaatac    1740
ctcgtggaga cgcagcgccc ggacggcggc tgggatgagc cgtactacac cggcacgggc    1800
ttcccagggg atttctacct cggctacacc atgtaccgcc acgtgtttcc gacgctcgcg    1860
ctcggccgct acaagcaagc catcgagcgc aggtga                              1896

<210> SEQ ID NO 13
<211> LENGTH: 1896
<212> TYPE: DNA
<213> ORGANISM: Artificial Sequence
<220> FEATURE:
<223> OTHER INFORMATION: mutant squalene-hopene
      cyclase_Polynucleotide_L607F

<400> SEQUENCE: 13
atggctgagc agttggtgga agcgccggcc tacgcgcgga cgctggatcg cgcggtggag      60
tatctcctct cctgccaaaa ggacgaaggc tactggtggg ggccgcttct gagcaacgtc     120
acgatggaag cggagtacgt cctcttgtgc cacattctcg atcgcgtcga tcgggatcgc     180
atggagaaga tccggcggta cctgttgcac gagcagcgcg aggacggcac gtgggccctg     240
tacccgggtg ggccgccgga cctcgacacg accatcgagg cgtacgtcgc gctcaagtat     300
atcggcatgt cgcgcgacga ggagccgatg cagaaggcgc tccggttcat tcagagccag     360
ggcgggatcg agtcgtcgcg cgtgttcacg cggatgtggc tggcgctggt gggagaatat     420
ccgtgggaga aggtgcccat ggtcccgccg gagatcatgt tcctcggcaa gcgcatgccg     480
ctcaacatct cgagtttggg ctcgtgggct cgggcgaccg tcgtggcgct tcgattgtg     540 atgagccgcc agccggtgtt cccgctgccc gagcgggcgc gcgtgcccga gctgtacgag     600
accgacgtgc tccgcgccg gcgcggcgcc aagggagggg gtgggtggat cttcgacgcg     660
ctcgaccggg cgctgcacgg gtatcagaag ctgtcggtgc acccgttccg ccgcgcggcc     720
gagatccgcg ccttggactg gttgctcgag cgccaggccg gagacggcag ctggggcggg     780
attcagccgc cttggtttta cgcgctcatc gcgctcaaga ttctcgacat gacgcagcat     840
ccggcgttca tcaagggctg ggaaggtcta gagctgtacg gcgtggagct ggattacgga     900
ggatggatgt ttcaggcttc catctcgccg gtgtgggaca cgggcctcgc cgtgctcgcg     960
ctgcgcgctg cggggcttcc ggccgatcac gaccgcttgg tcaaggcggg cgagtggctg    1020
ttggaccggc agatcacggt tccgggcgac tgggcggtga agcgcccgaa cctcaagccg    1080
ggcgggttcg cgttccagtt cgacaacgtg tactacccgg acgtggacga cacggccgtc    1140
gtggtgtggg cgctcaacac cctgcgcttg ccggacgagc gccgcaggcg ggacgccatg    1200
acgaagggat tccgctggat tgtcggcatg cagagctcga acggcggttg gggcgcctac    1260
```

```
gacgtcgaca acacgagcga tctcccgaac cacatcccgt tctgcgactt cggcgaagtg    1320
accgatccgc cgtcagagga cgtcaccgcc cacgtgctcg agtgtttcgg cagcttcggg    1380
tacgatgacg cctggaaggt catccggcgc gcggtggaat atctcaagcg ggagcagaag    1440
ccggacggca gctggttcgg tcgttggggc gtcaattacc tctacggcac gggcgcggtg    1500
gtgtcggcgc tgaaggcggt cgggatcgac acgcgcgagc cgtacattca aaaggcgctc    1560
gactgggtcg agcagcatca gaacccggac ggcggctggg gcgaggactg ccgctcgtac    1620
gaggatccgg cgtacgcggg taagggcgcg agcaccccgt cgcagacggc ctgggcgctg    1680
atggcgctca tcgcgggcgg cagggcggag tccgaggccg cgcgccgcgg cgtgcaatac    1740
ctcgtggaga cgcagcgccc ggacggcggc tgggatgagc cgtactacac cggcacgggc    1800
ttcccagggg atttctactt cggctacacc atgtaccgcc acgtgtttcc gacgctcgcg    1860
ctcggccgct acaagcaagc catcgagcgc aggtga    1896
```

<210> SEQ ID NO 14
<211> LENGTH: 1896
<212> TYPE: DNA
<213> ORGANISM: Artificial Sequence
<220> FEATURE:
<223> OTHER INFORMATION: mutant squalene-hopene
cyclase_Polynucleotide_L607W

<400> SEQUENCE: 14

```
atggctgagc agttggtgga agcgccggcc tacgcgcgga cgctggatcg cgcggtggag     60
tatctcctct cctgccaaaa ggacgaaggc tactggtggg ggccgcttct gagcaacgtc    120
acgatggaag cggagtacgt cctcttgtgc acattctcg atcgcgtcga tcgggatcgc    180
atggagaaga tccggcggta cctgttgcac gagcagcgcg aggacggcac gtgggccctg    240
tacccgggtg ggccgccgga cctcgacacg accatcgagg cgtacgtcgc gctcaagtat    300
atcggcatgt cgcgcgacga ggagccgatg cagaaggcgc tccggttcat tcagagccag    360
ggcgggatcg agtcgtcgcg cgtgttcacg cggatgtggc tggcgctggt gggagaatat    420
ccgtgggaga aggtgcccat ggtcccgccg gagatcatgt tcctcggcaa gcgcatgccg    480
ctcaacatct acgagtttgg ctcgtgggct cgggcgaccg tcgtggcgct tcgattgtg    540 atgagccgcc agccggtgtt cccgctgccc gagcgggcgc gcgtgcccga gctgtacgag    600
accgacgtgc tccgcgccg gcgcggcgcc aagggagggg gtgggtggat cttcgacgcg    660
ctcgaccggg cgctgcacgg gtatcagaag ctgtcggtgc acccgttccg ccgcgcggcc    720
gagatccgcg ccttggactg gttgctcgag cgccaggccg agacggcag ctggggcggg    780 attcagccgc cttggtttta cgcgctcatc gcgctcaaga ttctcgacat gacgcagcat    840
ccggcgttca tcaagggctg ggaaggtcta gagctgtacg gcgtggagct ggattacgga    900
ggatggatgt ttcaggcttc catctcgccg gtgtgggaca cgggcctcgc cgtgctcgcg    960
ctgcgcgctg cggggcttcc ggccgatcac gaccgcttgg tcaaggcggg cgagtggctg   1020
ttggaccggc agatcacggt tccgggcgac tgggcggtga agcgcccgaa cctcaagccg   1080
ggcgggttcg cgttccagtt cgacaacgtg tactacccgg acgtggacga cacggccgtc   1140
gtggtgtggg cgctcaacac cctgcgcttg ccggacgagc gccgcaggcg ggacgccatg   1200
acgaagggat tccgctggat tgtcggcatg cagagctcga acggcggttg gggcgcctac   1260
gacgtcgaca acacgagcga tctcccgaac cacatcccgt tctgcgactt cggcgaagtg   1320
accgatccgc cgtcagagga cgtcaccgcc cacgtgctcg agtgtttcgg cagcttcggg   1380
```

| | |
|---|---|
| tacgatgacg cctggaaggt catccggcgc gcggtggaat atctcaagcg ggagcagaag | 1440 |
| ccggacggca gctggttcgg tcgttggggc gtcaattacc tctacggcac gggcgcggtg | 1500 |
| gtgtcggcgc tgaaggcggt cgggatcgac acgcgcgagc cgtacattca aaaggcgctc | 1560 |
| gactgggtcg agcagcatca gaacccggac ggcggctggg gcgaggactg ccgctcgtac | 1620 |
| gaggatccgg cgtacgcggg taagggcgcg agcacccccgt cgcagacggc ctgggcgctg | 1680 |
| atggcgctca tcgcgggcgg cagggcgag tccgaggccg cgcgccgcgg cgtgcaatac | 1740 |
| ctcgtggaga cgcagcgccc ggacggcggc tgggatgagc cgtactacac cggcacgggc | 1800 |
| ttcccagggg atttctactg gggctacacc atgtaccgcc acgtgtttcc gacgctcgcg | 1860 |
| ctcggccgct acaagcaagc catcgagcgc aggtga | 1896 |

<210> SEQ ID NO 15
<211> LENGTH: 1896
<212> TYPE: DNA
<213> ORGANISM: Artificial Sequence
<220> FEATURE:
<223> OTHER INFORMATION: mutant squalene-hopene
cyclase_Polynucleotide_Y612A

<400> SEQUENCE: 15

| | |
|---|---|
| atggctgagc agttggtgga agcgccggcc tacgcgcgga cgctggatcg cgcggtggag | 60 |
| tatctcctct cctgccaaaa ggacgaaggc tactggtggg ggccgcttct gagcaacgtc | 120 |
| acgatggaag cggagtacgt cctcttgtgc cacattctcg atcgcgtcga tcgggatcgc | 180 |
| atggagaaga tccggcggta cctgttcac gagcagcgcg aggacggcac gtgggccctg | 240 |
| tacccgggtg ggccgccgga cctcgacacg accatcgagg cgtacgtcgc gctcaagtat | 300 |
| atcggcatgt cgcgcgacga ggagccgatg cagaaggcgc tccggttcat tcagagccag | 360 |
| ggcgggatcg agtcgtcgcg cgtgttcacg cggatgtggc tggcgctggt gggagaatat | 420 |
| ccgtgggaga aggtgcccat ggtcccgccg gagatcatgt tcctcggcaa gcgcatgccg | 480 |
| ctcaacatct acgagtttgg ctcgtgggct cgggcgaccg tcgtggcgct ctcgattgtg | 540 |
| atgagccgcc agccggtgtt cccgctgccc gagcgggcgc gcgtgcccga gctgtacgag | 600 |
| accgacgtgc tccgcgcccg gcgcggcgcc aagggagggg gtgggtggat cttcgacgcg | 660 |
| ctcgaccggg cgctgcacgg gtatcagaag ctgtcggtgc acccgttccg ccgcgcggcc | 720 |
| gagatccgcg ccttggactg gttgctcgag cgccaggccg agacggcag ctggggcggg | 780 |
| attcagccgc cttggtttta cgcgctcatc gcgctcaaga ttctcgacat gacgcagcat | 840 |
| ccggcgttca tcaagggctg ggaaggtcta gagctgtacg gcgtggagct ggattacgga | 900 |
| ggatggatgt ttcaggcttc catctcgccg gtgtgggaca cgggcctcgc cgtgctcgcg | 960 |
| ctgcgcgctg cggggcttcc ggccgatcac gaccgcttgg tcaaggcggg cgagtggctg | 1020 |
| ttggaccggc agatcacggt tccgggcgac tgggcggtga agcgcccgaa cctcaagccg | 1080 |
| ggcgggttcg cgttccagtt cgacaacgtg tactacccgg acgtgacga cacggccgtc | 1140 |
| gtggtgtggg cgctcaacac cctgcgcttg ccggacgagc gccgcaggcg ggacgccatg | 1200 |
| acgaagggat ccgctggat tgtcggcatg cagagctcga acggcggttg gggcgcctac | 1260 |
| gacgtcgaca cacgagcga tctcccgaac acatcccgt tctgcgactt cggcgaagtg | 1320 |
| accgatccgc cgtcagagga cgtcaccgcc cacgtgctcg agtgtttcgg cagcttcggg | 1380 |
| tacgatgacg cctggaaggt catccggcgc gcggtggaat atctcaagcg ggagcagaag | 1440 |
| ccggacggca gctggttcgg tcgttggggc gtcaattacc tctacggcac gggcgcggtg | 1500 |

-continued

```
gtgtcggcgc tgaaggcggt cgggatcgac acgcgcgagc cgtacattca aaaggcgctc      1560
gactgggtcg agcagcatca gaacccggac ggcggctggg gcgaggactg ccgctcgtac      1620
gaggatccgg cgtacgcggg taagggcgcg agcacccccgt cgcagacggc ctgggcgctg      1680
atggcgctca tcgcgggcgg cagggcggag tccgaggccg cgcgccgcgg cgtgcaatac      1740
ctcgtggaga cgcagcgccc ggacggcggc tgggatgagc cgtactacac cggcacgggc      1800
ttcccagggg atttctacct cggctacacc atggcccgcc acgtgtttcc gacgctcgcg      1860
ctcggccgct acaagcaagc catcgagcgc aggtga                                1896
```

<210> SEQ ID NO 16
<211> LENGTH: 625
<212> TYPE: PRT
<213> ORGANISM: Bacillus megaterium

<400> SEQUENCE: 16

```
Met Ile Ile Leu Leu Lys Glu Val Gln Leu Glu Ile Gln Arg Arg Ile
1               5                   10                  15

Ala Tyr Leu Arg Pro Thr Gln Lys Asn Asp Gly Ser Phe Arg Tyr Cys
                20                  25                  30

Phe Glu Thr Gly Val Met Pro Asp Ala Phe Leu Ile Met Leu Leu Arg
            35                  40                  45

Thr Phe Asp Leu Asp Lys Glu Val Leu Ile Lys Gln Leu Thr Glu Arg
        50                  55                  60

Ile Val Ser Leu Gln Asn Glu Asp Gly Leu Trp Thr Leu Phe Asp Asp
65                  70                  75                  80

Glu Glu His Asn Leu Ser Ala Thr Ile Gln Ala Tyr Thr Ala Leu Leu
                85                  90                  95

Tyr Ser Gly Tyr Tyr Gln Lys Asn Asp Arg Ile Leu Arg Lys Ala Glu
            100                 105                 110

Arg Tyr Ile Ile Asp Ser Gly Gly Ile Ser Arg Ala His Phe Leu Thr
        115                 120                 125

Arg Trp Met Leu Ser Val Asn Gly Leu Tyr Glu Trp Pro Lys Leu Phe
    130                 135                 140

Tyr Leu Pro Leu Ser Leu Leu Val Pro Thr Tyr Val Pro Leu Asn
145                 150                 155                 160

Phe Tyr Glu Leu Ser Thr Tyr Ala Arg Ile His Phe Val Pro Met Met
                165                 170                 175

Val Ala Gly Asn Lys Lys Phe Ser Leu Thr Ser Arg His Thr Pro Ser
            180                 185                 190

Leu Ser His Leu Asp Val Arg Glu Gln Lys Gln Ser Glu Glu Thr
        195                 200                 205

Thr Gln Glu Ser Arg Ala Ser Ile Phe Leu Val Asp His Leu Lys Gln
    210                 215                 220

Leu Ala Ser Leu Pro Ser Tyr Ile His Lys Leu Gly Tyr Gln Ala Ala
225                 230                 235                 240

Glu Arg Tyr Met Leu Glu Arg Ile Glu Lys Asp Gly Thr Leu Tyr Ser
                245                 250                 255

Tyr Ala Thr Ser Thr Phe Phe Met Ile Tyr Gly Leu Leu Ala Leu Gly
            260                 265                 270

Tyr Lys Lys Asp Ser Phe Val Ile Gln Lys Ala Ile Asp Gly Ile Cys
        275                 280                 285

Ser Leu Leu Ser Thr Cys Ser Gly His Val His Val Glu Asn Ser Thr
    290                 295                 300
```

Ser Thr Val Trp Asp Thr Ala Leu Leu Ser Tyr Ala Leu Gln Glu Ala
305                 310                 315                 320

Gly Val Pro Gln Gln Asp Pro Met Ile Lys Gly Thr Thr Arg Tyr Leu
            325                 330                 335

Lys Lys Arg Gln His Thr Lys Leu Gly Asp Trp Gln Phe His Asn Pro
            340                 345                 350

Asn Thr Ala Pro Gly Gly Trp Gly Phe Ser Asp Ile Asn Thr Asn Asn
            355                 360                 365

Pro Asp Leu Asp Asp Thr Ser Ala Ala Ile Arg Ala Leu Ser Arg Arg
370                 375                 380

Ala Gln Thr Asp Thr Asp Tyr Leu Glu Ser Trp Gln Arg Gly Ile Asn
385                 390                 395                 400

Trp Leu Leu Ser Met Gln Asn Lys Asp Gly Gly Phe Ala Ala Phe Glu
                405                 410                 415

Lys Asn Thr Asp Ser Ile Leu Phe Thr Tyr Leu Pro Leu Glu Asn Ala
                420                 425                 430

Lys Asp Ala Ala Thr Asp Pro Ala Thr Ala Asp Leu Thr Gly Arg Val
                435                 440                 445

Leu Glu Cys Leu Gly Asn Phe Ala Gly Met Asn Lys Ser His Pro Ser
450                 455                 460

Ile Lys Ala Ala Val Lys Trp Leu Phe Asp His Gln Leu Asp Asn Gly
465                 470                 475                 480

Ser Trp Tyr Gly Arg Trp Gly Val Cys Tyr Ile Tyr Gly Thr Trp Ala
                485                 490                 495

Ala Ile Thr Gly Leu Arg Ala Val Gly Val Ser Ala Ser Asp Pro Arg
                500                 505                 510

Ile Ile Lys Ala Ile Asn Trp Leu Lys Ser Ile Gln Gln Glu Asp Gly
                515                 520                 525

Gly Phe Gly Glu Ser Cys Tyr Ser Ala Ser Leu Lys Lys Tyr Val Pro
                530                 535                 540

Leu Ser Phe Ser Thr Pro Ser Gln Thr Ala Trp Ala Leu Asp Ala Leu
545                 550                 555                 560

Met Thr Ile Cys Pro Leu Lys Asp Arg Ser Val Glu Lys Gly Ile Lys
                565                 570                 575

Phe Leu Leu Asn Pro Asn Leu Thr Glu Gln Gln Thr His Tyr Pro Thr
                580                 585                 590

Gly Ile Gly Leu Pro Gly Gln Phe Tyr Ile Gln Tyr His Ser Tyr Asn
                595                 600                 605

Asp Ile Phe Pro Leu Leu Ala Leu Ala His Tyr Ala Lys Lys His Ser
610                 615                 620

Ser
625

<210> SEQ ID NO 17
<211> LENGTH: 632
<212> TYPE: PRT
<213> ORGANISM: Bacillus subtilis

<400> SEQUENCE: 17

Met Gly Thr Leu Gln Glu Lys Val Arg Arg Tyr Gln Lys Thr Ile
1               5                   10                  15

Ala Glu Leu Lys Asn Arg Gln Asn Ala Asp Gly Ser Trp Thr Phe Cys
                20                  25                  30

Phe Glu Gly Pro Ile Met Thr Asn Ser Phe Phe Ile Leu Leu Leu Thr
            35                  40                  45

```
Ser Leu Asp Glu Gly Glu Asn Glu Lys Glu Leu Ile Ser Ala Leu Ala
    50                  55                  60

Ala Gly Ile Arg Glu Lys Gln Gln Pro Asp Gly Thr Phe Ile Asn Tyr
65                  70                  75                  80

Pro Asp Glu Thr Ser Gly Asn Ile Thr Ala Thr Val Gln Gly Tyr Val
                85                  90                  95

Gly Met Leu Ala Ser Gly Cys Phe His Arg Ser Asp Pro His Met Arg
            100                 105                 110

Lys Ala Glu Gln Ser Ile Ile Ser His Gly Gly Leu Arg His Val His
            115                 120                 125

Phe Met Thr Lys Trp Met Leu Ala Val Asn Gly Leu Tyr Pro Trp Pro
    130                 135                 140

Val Leu Tyr Leu Pro Leu Ser Leu Met Ala Leu Pro Pro Thr Leu Pro
145                 150                 155                 160

Val His Phe Tyr Gln Phe Ser Ala Tyr Ala Arg Ile His Phe Ala Pro
                165                 170                 175

Met Ala Val Thr Leu Asn Gln Arg Phe Val Leu Lys Asn Arg Asn Ile
            180                 185                 190

Pro Ser Leu Arg His Leu Asp Pro His Met Thr Lys Asn Pro Phe Thr
            195                 200                 205

Trp Leu Arg Ser Asp Ala Phe Glu Glu Arg Asp Leu Thr Ser Ile Trp
    210                 215                 220

Ser His Trp Asn Arg Ile Phe His Ala Pro Phe Ala Phe Gln Gln Leu
225                 230                 235                 240

Gly Leu Gln Thr Ala Lys Thr Tyr Met Leu Asp Arg Ile Glu Lys Asp
                245                 250                 255

Gly Thr Leu Tyr Ser Tyr Ala Ser Ala Thr Ile Phe Met Val Tyr Ser
            260                 265                 270

Leu Leu Ser Leu Gly Val Ser Arg Tyr Ser Pro Val Ile Lys Arg Ala
    275                 280                 285

Ile Asn Gly Ile Lys Ser Leu Met Thr Lys Cys Asn Gly Ile Pro Tyr
290                 295                 300

Leu Glu Asn Ser Thr Ser Thr Val Trp Asp Thr Ala Leu Ile Ser Tyr
305                 310                 315                 320

Ala Leu Gln Lys Asn Gly Val Thr Glu Thr Asp Gly Ser Ile Thr Lys
                325                 330                 335

Ala Ala Ala Tyr Leu Leu Glu Arg Gln His Thr Lys Arg Ala Asp Trp
            340                 345                 350

Ser Val Lys Asn Pro Ser Ala Ala Pro Gly Gly Trp Gly Phe Ser Asn
    355                 360                 365

Ile Asn Thr Asn Asn Pro Asp Cys Asp Asp Thr Ala Ala Val Leu Lys
    370                 375                 380

Ala Ile Pro His Ser Tyr Ser Pro Ser Ala Trp Glu Arg Gly Val Ser
385                 390                 395                 400

Trp Leu Leu Ser Met Gln Asn Asn Asp Gly Gly Phe Ser Ala Phe Glu
                405                 410                 415

Lys Asn Val Asn His Pro Leu Ile Arg Leu Leu Pro Leu Glu Ser Ala
            420                 425                 430

Glu Asp Ala Ala Val Asp Pro Ser Thr Ala Asp Leu Thr Gly Arg Val
            435                 440                 445

Leu His Phe Leu Gly Glu Lys Ala Gly Phe Thr Glu Lys His Gln His
    450                 455                 460
```

```
Ile Gln Arg Ala Val Asn Trp Leu Phe Glu His Glu Gln Asn Gly
465                 470                 475                 480

Ser Trp Tyr Gly Arg Trp Gly Val Cys Tyr Ile Tyr Gly Thr Trp Ala
                485                 490                 495

Ala Leu Thr Gly Met His Ala Cys Glu Val Asp Arg Lys His Pro Ala
            500                 505                 510

Ile Gln Lys Ala Leu Arg Trp Leu Lys Ser Ile Gln His Asp Asp Gly
        515                 520                 525

Ser Trp Gly Glu Ser Cys Asn Ser Ala Glu Val Lys Thr Tyr Val Pro
    530                 535                 540

Leu His Lys Gly Thr Ile Val Gln Thr Ala Trp Ala Leu Asp Ala Leu
545                 550                 555                 560

Leu Thr Tyr Glu Ser Ser Glu His Pro Ser Val Val Lys Gly Met Gln
                565                 570                 575

Tyr Leu Thr Asp Ser Ser Tyr His Gly Ala Asp Ser Leu Ala Tyr Pro
            580                 585                 590

Ala Gly Ile Gly Leu Pro Lys Gln Phe Tyr Ile Arg Tyr His Ser Tyr
        595                 600                 605

Pro Tyr Val Phe Ser Leu Leu Ala Val Gly Lys Tyr Leu Asn Ser Ile
    610                 615                 620

Glu Lys Glu Thr Ala Asn Glu Thr
625                 630

<210> SEQ ID NO 18
<211> LENGTH: 592
<212> TYPE: PRT
<213> ORGANISM: Bacillus licheniformis

<400> SEQUENCE: 18

Met Thr Asp Ser Phe Phe Ile Leu Met Leu Thr Ser Leu Gly Asp Gln
1               5                   10                  15

Asp Ser Ser Leu Ile Ala Ser Leu Ala Glu Arg Ile Arg Ser Arg Gln
            20                  25                  30

Ser Glu Asp Gly Ala Phe Arg Asn His Pro Asp Glu Arg Ala Gly Asn
        35                  40                  45

Leu Thr Ala Thr Val Gln Gly Tyr Thr Gly Met Leu Ala Ser Gly Leu
    50                  55                  60

Tyr Asp Arg Lys Ala Pro His Met Gln Lys Ala Glu Ala Phe Ile Lys
65                  70                  75                  80

Asp Ala Gly Gly Leu Lys Gly Val His Phe Met Thr Lys Trp Met Leu
                85                  90                  95

Ala Ala Asn Gly Leu Tyr Pro Trp Pro Arg Ala Tyr Ile Pro Leu Ser
            100                 105                 110

Phe Leu Leu Ile Pro Ser Tyr Phe Pro Leu His Phe His Phe Ser
        115                 120                 125

Thr Tyr Ala Arg Ile His Phe Val Pro Met Ala Ile Thr Phe Asn Arg
    130                 135                 140

Arg Phe Ser Leu Lys Asn Asn Gln Ile Gly Ser Leu Arg His Leu Asp
145                 150                 155                 160

Glu Ala Met Ser Lys Asn Pro Leu Glu Trp Leu Asn Ile Arg Ala Phe
                165                 170                 175

Asp Glu Arg Thr Phe Tyr Ser Phe Asn Leu Gln Trp Lys Gln Leu Phe
            180                 185                 190

Gln Trp Pro Ala Tyr Val His Gln Leu Gly Phe Glu Ala Gly Lys Lys
        195                 200                 205
```

Tyr Met Leu Asp Arg Ile Glu Glu Asp Gly Thr Leu Tyr Ser Tyr Ala
    210                 215                 220

Ser Ala Thr Met Phe Met Ile Tyr Ser Leu Leu Ala Met Gly Ile Ser
225                 230                 235                 240

Lys Asn Ala Pro Val Val Lys Ala Val Ser Gly Ile Lys Ser Leu
                245                 250                 255

Ile Ser Ser Cys Gly Lys Glu Gly Ala His Leu Glu Asn Ser Thr Ser
                260                 265                 270

Thr Val Trp Asp Thr Ala Leu Ile Ser Tyr Ala Met Gln Glu Ser Gly
            275                 280                 285

Val Pro Glu Gln His Ser Ser Thr Ser Ser Ala Ala Asp Tyr Leu Leu
    290                 295                 300

Lys Arg Gln His Val Lys Lys Ala Asp Trp Ala Val Ser Asn Pro Gln
305                 310                 315                 320

Ala Val Pro Gly Gly Trp Gly Phe Ser His Ile Asn Thr Asn Pro
                325                 330                 335

Asp Leu Asp Asp Thr Ala Ala Ala Leu Lys Ala Ile Pro Phe Gln Arg
                340                 345                 350

Arg Pro Asp Ala Trp Asn Arg Gly Leu Ala Trp Leu Leu Ser Met Gln
            355                 360                 365

Asn Lys Asp Gly Gly Phe Ala Ala Phe Glu Lys Asp Val Asp His Pro
    370                 375                 380

Leu Ile Arg Asn Leu Pro Leu Glu Ser Ala Ala Glu Ala Ala Val Asp
385                 390                 395                 400

Pro Ser Thr Ala Asp Leu Thr Gly Arg Val Leu His Leu Leu Gly Leu
                405                 410                 415

Lys Gly Arg Phe Thr Asp Asn His Pro Ala Val Arg Arg Ala Leu Arg
                420                 425                 430

Trp Leu Asp His His Gln Lys Ala Asp Gly Ser Trp Tyr Gly Arg Trp
            435                 440                 445

Gly Val Cys Phe Ile Tyr Gly Thr Trp Ala Ala Leu Thr Gly Met Lys
    450                 455                 460

Ala Val Gly Val Ser Ala Asn Gln Thr Ser Val Lys Lys Ala Ile Ser
465                 470                 475                 480

Trp Leu Lys Ser Ile Gln Arg Glu Asp Gly Ser Trp Gly Glu Ser Cys
                485                 490                 495

Lys Ser Cys Glu Ala Lys Arg Phe Val Pro Leu His Phe Gly Thr Val
                500                 505                 510

Val Gln Ser Ser Trp Ala Leu Glu Ala Leu Leu Gln Tyr Glu Arg Pro
            515                 520                 525

Asp Asp Pro Gln Ile Ile Lys Gly Ile Arg Phe Leu Ile Asp Glu His
    530                 535                 540

Glu Ser Ser Arg Glu Arg Leu Glu Tyr Pro Thr Gly Ile Gly Leu Pro
545                 550                 555                 560

Asn Gln Phe Tyr Ile Arg Tyr His Ser Tyr Pro Phe Val Phe Ser Leu
                565                 570                 575

Leu Ala Ser Ser Ala Phe Ile Lys Lys Ala Glu Met Arg Glu Thr Tyr
                580                 585                 590

<210> SEQ ID NO 19
<211> LENGTH: 1878
<212> TYPE: DNA
<213> ORGANISM: Bacillus megaterium

<400> SEQUENCE: 19

```
gtgatcatat tgctaaagga agttcagcta gagattcagc gaagaatcgc ctatctgcgc        60
ccaacacaaa aaaatgacgg gtcatttcgc tactgttttg aaacaggcgt tatgcctgat       120
gcgttttaa ttatgcttct tcgcaccttt gatttagata agaagtgtt gattaaacaa         180
ttaaccgaac ggattgtttc ccttcaaaat gaagatggtc tttggacgtt gtttgatgat       240
gaagaacata acttatccgc cactattcaa gcttatacag ctctttttata ttcagggtat      300
taccaaaaaa acgaccggat tttgcgaaaa gcagaaagat atattataga ttcaggaggc       360
atttcgcgcg ctcatttcct cacaagatgg atgctttctg ttaacggttt atacgagtgg       420
ccaaagctat tttacctccc gctttctctt ttgctcgtgc ctacctatgt accgcttaac       480
tttatgaat taagcactta tgccagaatt cacttcgttc cgatgatggt agcaggaaac        540
aaaaaatttt cacttacttc taggcataca ccttctcttt ctcatttaga tgtaagagaa       600
cagaaacagg aatcggagga aactactcaa gaatcacgcg cttcaatttt tttagtcgac       660
catttaaaac agctggcttc tttaccttct tacatccaca aacttggtta tcaagcagcc       720
gagcgttaca tgctagaaag aattgaaaaa gatggaacac tctacagcta cgccacctct       780
acttttttta tgatttacgg tcttttggct cttggctata aaaagattc atttgtgatc        840
caaaaagcaa ttgacgggat ttgttcacta cttagtacat gcagcggcca cgtgcacgta       900
gaaaactcca cgtcaaccgt ttgggatacc gcgctgctct cttatgctct acaggaagca       960
ggtgtaccgc agcaagatcc catgattaaa ggcacaactc gctacttaaa gaaaagacag      1020
catacaaagc ttggagattg gcagtttcat aacccaaata cagcacctgg aggctgggg       1080
ttttccgata ttaatacaaa taaccctgac ttagacgata cgtctgctgc tatcagagca      1140
ctttctagaa gagcacaaac cgatacagat tatttggagt cttggcaaag agggattaac      1200
tggctgctgt ccatgcaaaa caaagatggg ggttttgctg catttgaaaa aaataccgac      1260
tctattttat ttacttatct gccgcttgaa atgcaaaag atgcagcgac ggatccggct       1320
actgccgatt taaccggtcg agtgcttgag tgtctcggaa actttgctgg tatgaataaa      1380
tcccacccct tcgattaaagc tgcagtaaaa tggttgtttg atcatcaatt ggataacggg     1440
agctggtacg gccggtgggg agtttgctat atttacggaa cgtgggccgc tattacagga      1500
ctccgtgctg tagggggttc tgcttctgat ccgcgtatca tcaaagctat caactggctc      1560
aaaagcattc aacaagaaga cggtggattc ggagaatcat gctatagcgc ttcttttaaaa     1620
aaatatgtgc cactatcgtt tagcaccccct tctcaaacgg cttgggctct cgatgctta     1680
atgacaatat gtccgttaaa agatcgatcc gttgaaaaag gaattaaatt tttactgaat      1740
ccaaatctta cagagcagca aactcattac cccacgggaa ttggtcttcc tggacaattt      1800
tatattcagt accacagcta caatgatatt tttcctcttc ttgcacttgc ccactacgca      1860
aaaaaacatt cttcgtaa                                                     1878
```

<210> SEQ ID NO 20
<211> LENGTH: 1899
<212> TYPE: DNA
<213> ORGANISM: Bacillus subtilis

<400> SEQUENCE: 20

```
atgggcacac ttcaggagaa agtgaggcgt tatcaaaaga aaaccattgc agagttaaaa        60
aacaggcaaa atgctgacgg ttcgtggaca ttttgctttg aaggaccaat catgacaaat       120
tccttttttta ttttgctcct cacctcacta gatgaaggcg agaatgaaaa agaactaata     180
```

```
tcagcgcttg cagccggcat tcgtgaaaaa cagcagcccg acggcacatt catcaattat       240
cccgatgaaa cgagcggtaa tataacggct accgtccaag gatatgtcgg gatgctggct       300
tcaggttgtt ttcaccgatc tgacccgcac atgaggaaag ctgaacaatc tatcatctca       360 catgcggtt tgagacatgt tcatttcatg acaaaatgga tgcttgccgt gaacgggctg        420
tatccttggc ctgtcttgta tttaccatta tcactcatgg cgctcccccc aacgttacca       480
gttcatttct atcagttcag cgcatatgcc cgaattcatt ttgctcctat ggctgtaaca       540
ctcaatcagc gatttgttct taaaaaccgc aatattccat ctcttcgcca tctcgatccg       600
cacatgacaa aaacccttt cacttggctt cgatcagatg cttttgaaga aagagatctc        660
acgtctattt ggtcacattg aatcgcatt ttccatgcac cctttgcttt tcagcagctc        720
ggcttacaga cggctaaaac atatatgctg gaccggattg aaaaagacgg aacattatac       780
agctacgcaa gcgcaaccat atttatggtt tacagccttc tgtcacttgg tgtgtcacgc       840
tactctcctg ttatcaagag ggcgattaac ggcatcaaat cactgatgac aaagtgcaac       900
gggattcctt atctggaaaa ctctacttca actgtttggg atacagcttt gatcagctat       960
gcccttcaaa aaacggcgt gaccgaaaca gacggctcta ttacaaaagc agctgcctat      1020
ttgctagaac gccagcatac caaaagagca gattggtctg tcaaaaaccc gagtgcagcg      1080
cccggcggct ggggcttttc aaacatcaat acaaataacc ctgactgtga cgacactgca      1140
gccgtattaa aagcgattcc ccacagttat tctccttcgg cttgggagcg aggggtgtct      1200 tggctttat cgatgcaaaa caatgacggc ggattttctg cttttgaaaa aaatgtgaac       1260
catcctctaa ttcgccttct cccgcttgaa tccgccgagg acgcggcagt tgacccttca      1320
accgctgacc tcaccggacg tgtgctgcac tttttaggcg agaaagctgg tttcactgag      1380
aaacatcaac atattcagcg cgctgtgaac tggcttttcg aacatcaaga acaaaatggg      1440
tcatggtacg ggagatgggg tgtttgctac atttacggca catgggctgc tctcacgggt      1500
atgcatgcct gcgaagttga ccgaaagcac cctgctatac aaaaggcctt gcgctggctc      1560
aaatccatac agcatgatga cggcagctgg ggagaatcct gtaatagcgc cgaagtcaaa      1620
acgtacgtcc cgcttcataa aggaaccatt gtacaaacgg cctgggcttt agacgctttg      1680
ctcacatacg aaagttccga acacccatct gttgtgaaag gcatgcaata ccttactgac      1740
agcagttatc atggcgccga tagcttggcc tatccagccg gaatcggatt gccaaagcaa      1800
ttttatatcc gctatcacag ttatccatat gtattctctt tgctggctgt cgggaagtat      1860
ttgaattcta tcgaaaagga gacagcaaat gaaacgtga                             1899

<210> SEQ ID NO 21
<211> LENGTH: 1779
<212> TYPE: DNA
<213> ORGANISM: Bacillus licheniformis

<400> SEQUENCE: 21
atgacggaca gttttttcat tctgatgctg acatcactcg gcgatcagga ctcttctctc        60
atcgcaagtc ttgctgaacg aatccgttca aggcagagcg aagacggcgc gtttcgcaat       120
cacccggatg aaagagcagg caatctgacc gcgacagtcc aggctatac cggaatgctg        180 gcttcggggc tctatgaccg gaaagctccg catatgcaga aagccgaagc ttttattaag       240
gacgcaggcg gattgaaggg cgtccacttt atgacgaagt ggatgctcgc cgccaacggt       300
ctgtatccat ggccgagagc ctatattccg ctctcgtttt tgctgatccc gtcctatttc       360
```

-continued

```
ccgctgcatt tttaccattt cagcacatac gcaagaattc attttgtccc catggccatt      420
acgtttaatc ggcgattctc tttaaaaaac aaccaaatcg gctcgcttcg gcacctggat      480
gaagccatgt caaaaaaccc tctcgaatgg ctgaacatcc gcgcctttga cgaaagaacc      540
ttctattctt tcaatctgca atggaaacag ctctttcaat ggccggctta cgtccatcag      600
ctcggatttg aggccggcaa aaaatatatg ctggacagaa tcgaagaaga cggaacgcta      660
tacagctatg cgagcgcgac catgttcatg atttacagcc tgcttgcgat gggaatatct      720
aaaaacgccc ccgttgtcaa aaaagcagtc agcggaatca aaagtcttat ttcatcatgc      780
ggaaaggaag gggcccattt ggaaaactca acttccaccg tctgggatac ggccctcatc      840
agctatgcca tgcaggaatc cggagtgcct gaacaacatt cttccacctc atcggcagcc      900
gactaccttc tcaaaagaca gcatgtgaaa aaagcggact gggctgtctc aaatcctcaa      960
gcggtccctg gcgggtgggg ttttcacac atcaatacaa acaatcccga tttggacgat     1020
accgctgcgg cattaaaagc tattccgttt caacggcgtc cggatgcatg gaaccggggg     1080
ctcgcctggc ttttatccat gcaaaacaag gacggagggt ttgcggcatt tgaaaaagat     1140
gttgaccatc cgcttattcg aaatctgccg ctcgaatctg ccgctgaggc agcagtcgat     1200
ccgtcaacgg cagacttgac cggacgcgtt cttcatctgc tcgggcttaa agggcggttc     1260
acagataacc atcctgcggt ccggcgcgcc ctcaggtggc ttgatcatca tcagaaagcg     1320
gacggctctt ggtatggcag atggggcgtc tgctttattt acggtacatg ggccgcactc     1380
accggtatga aagctgtcgg ggtttccgcc aaccagacgt ctgtcaaaaa agcgatctcc     1440
tggctaaaat cgatccagcg tgaagacgga agctggggag aatcttgcaa aagctgtgaa     1500
gcgaagcgtt ttgtccctct tcactttgga acagttgttc aatcttcatg ggcgctggag     1560
gcgcttttgc aatatgagcg tccggatgac ccacagatca taaaagggat ccgtttctc     1620 atcgatgaac acgaaagctc gcgtgagcga ctcgaatacc cgacgggaat cgggctgccg     1680
aaccaattct acatccgcta tcacagttat ccttttgtgt tttcattgct cgcttcaagc     1740
gcatttatta aaaagcgga aatgagggag acatattga                            1779
```